United States Patent
Okamoto et al.

[11] Patent Number: 5,969,178
[45] Date of Patent: Oct. 19, 1999

[54] USING METHACROLEIN AND METHANOL AS DEHYDRATION AND ABSORPTION AGENTS DURING PRODUCTION OF METHYL METHACRYLATE

[75] Inventors: Hiroshige Okamoto, Okayama; Hideaki Goto, Kurashiki, both of Japan

[73] Assignee: Asahi Kasei Kogyo Kabushiki Kaisha, Osaka, Japan

[21] Appl. No.: 09/110,695

[22] Filed: Jul. 7, 1998

[30] Foreign Application Priority Data

Jul. 8, 1997 [JP] Japan ................................. 9-181964

[51] Int. Cl.⁶ .................................................. C07O 67/00
[52] U.S. Cl. ............................................. 560/208; 560/210
[58] Field of Search ..................................... 560/208, 210

[56] References Cited

U.S. PATENT DOCUMENTS

| | | |
|---|---|---|
| 2,514,966 | 7/1950 | Pierotti et al. . |
| 4,249,019 | 2/1981 | Tamura et al. . |
| 4,329,513 | 5/1982 | Aoshima et al. . |
| 4,518,462 | 5/1985 | Aoshima et al. . |

FOREIGN PATENT DOCUMENTS

| | | |
|---|---|---|
| 49-92007 | 9/1974 | Japan . |
| 55-19213 | 2/1980 | Japan . |
| 56-87530 | 7/1981 | Japan . |
| 57-9739 | 1/1982 | Japan . |
| 57-9740 | 1/1982 | Japan . |
| 57-35856 B2 | 7/1982 | Japan . |
| 57-35857 B2 | 7/1982 | Japan . |
| 57-35859 B2 | 7/1982 | Japan . |
| 58-157740 | 9/1983 | Japan . |
| 62-7902 B2 | 2/1987 | Japan . |
| 5-69813 B2 | 10/1993 | Japan . |

*Primary Examiner*—Gary Geist
*Assistant Examiner*—Robert W. Deemie
*Attorney, Agent, or Firm*—Pennie & Edmonds LLP

[57] ABSTRACT

Disclosed is a method for producing methyl methacrylate, which comprises: subjecting isobutylene and/or tert-butanol to a gas phase catalytic oxidation reaction with molecular oxygen to thereby obtain gas (a) containing methacrolein gas and steam; introducing gas (a) and a methacrolein/methanol liquid mixture (I) into a dehydration tower at a lower portion thereof and at an upper portion thereof, respectively, thereby allowing the liquid mixture (I) to flow downwardly in the dehydration tower and contact countercurrently with the gas (a) in the dehydration tower, to thereby obtain a dehydrated gas mixture (b) containing methacrolein gas and methanol gas; introducing the dehydrated gas mixture (b) and a methacrolein/methanol liquid mixture (II) into an absorption tower at a lower portion thereof and at an upper portion thereof, respectively, thereby allowing the liquid mixture (II) to flow downwardly and contact countercurrently with the dehydrated gas mixture (b) in the absorption tower, thereby obtaining a methacrolein/methanol liquid mixture (III); and introducing the liquid mixture (III) into a reactor and subjecting the methacrolein and methanol, which are contained in the liquid mixture (III), to an oxidative esterification reaction in the reactor in the presence of molecular oxygen and in the presence of a palladium catalyst.

9 Claims, 2 Drawing Sheets

USING METHACROLEIN AND METHANOL AS DEHYDRATION AND ABSORPTION AGENTS DURING PRODUCTION OF METHYL METHACRYLATE

BACKGROUND OF THE INVENTION

1. Field of The Invention

The present invention relates to a method for producing methyl methacrylate. More particularly, the present invention is concerned with a method for producing methyl methacrylate, which comprises subjecting at least one starting material selected from the group consisting of isobutylene and tert-butanol to a gas phase catalytic oxidation reaction with molecular oxygen in the presence of a catalyst to thereby obtain gas (a) containing methacrolein gas and steam; introducing the gas (a) and a liquid mixture (I) containing liquid methacrolein and liquid methanol into a dehydration tower at a lower portion thereof and at an upper portion thereof, respectively, thereby allowing the liquid mixture (I) to flow downwardly in the dehydration tower and contact countercurrently with the gas (a) in the dehydration tower, to thereby obtain a dehydrated gas mixture (b) containing methacrolein gas and methanol gas; introducing the dehydrated gas mixture (b) and a liquid mixture (II) containing liquid methacrolein and liquid methanol into an absorption tower at a lower portion thereof and at an upper portion thereof, respectively, thereby allowing the liquid mixture (II) to flow downwardly in the absorption tower and contact countercurrently with the dehydrated gas mixture (b) in the absorption tower, so that substantially all of the methacrolein gas and methanol gas which are contained in the dehydrated gas mixture (b) is absorbed by the liquid mixture (II), thereby obtaining a liquid mixture (III) containing liquid methacrolein and liquid methanol; and subjecting the methacrolein and methanol, which are contained in the liquid mixture (III), to an oxidative esterification reaction in the presence of molecular oxygen and in the presence of a palladium catalyst.

By the method of the present invention, it has become possible to provide a methacrolein/methanol liquid mixture for an oxidative esterification reaction, which has a high methacrolein content, as compared to the methacrolein content of the methacrolein/methanol liquid mixtures provided by the conventional methods. Therefore, by the method of the present invention, methyl methacrylate can be produced with high efficiency. Further, in the method of the present invention, each of the above-mentioned liquid mixtures (I) and (II) introduced into the dehydration tower and the absorption tower, respectively, may individually be a liquid mixture (IV) containing liquid methacrolein and liquid methanol, which is obtained by separation from the reaction mixture produced by the above-mentioned oxidative esterification reaction. Therefore, in the method of the present invention, when the production of methyl methacrylate is continuously performed by recycling the liquid mixture (IV) (which is separated from the reaction mixture obtained by the oxidative esterification reaction) as the liquid mixtures (I) and/or (II), the amount of methanol needed for the continuous production process can be considerably reduced, as compared to that in the conventional methods, and the continuous production process can be performed without using complicated apparatuses for the separation and recovery of methanol, which are necessarily used in the conventional methods. This is advantageous not only in that the cost of producing methyl methacrylate can be considerably reduced, but also in that the production process is free from the troubles caused by the use of the complicated apparatuses for the separation and recovery of methanol, so that the desired methyl methacrylate can be produced stably.

2. Prior Art

For producing methyl methacrylate, which has a high commercial value, a so-called "via methacrylic acid process" has already been practiced on a commercial scale. The "via methacrylic acid process" comprises subjecting at least one starting material selected from the group consisting of isobutylene and tert-butanol to a gas phase catalytic oxidation reaction in the presence of molecular oxygen and in the presence of a catalyst to thereby obtain methacrolein; subjecting the obtained methacrolein to a gas phase catalytic oxidation reaction in the presence of molecular oxygen and in the presence of a catalyst to thereby obtain methacrylic acid; and reacting the obtained methacrylic acid with methanol to obtain methyl methacrylate.

On the other hand, recently, extensive and intensive studies have been made on a newly developed method for producing methyl methacrylate, which comprises subjecting methacrolein (ML) and methanol (MeOH) to an oxidative esterification reaction in the presence of molecular oxygen and in the presence of a catalyst, to thereby produce methyl methacrylate (MMA) by one step directly from methacrolein (ML) (this process is hereafter frequently referred to simply as a "direct ML-to-MMA process" and the above-mentioned oxidative esterification reaction is hereafter frequently referred to simply as a "direct ML-to-MMA synthesis reaction"?).

In this process (i.e., the direct ML-to-MMA process), a liquid mixture of liquid methacrolein and liquid methanol is introduced into a reactor, and a reaction is performed in the presence of molecular oxygen and in the presence of a palladium catalyst. However, the activity of the palladium catalyst used in this process is likely to be inhibited by water contained in the reaction system. Therefore, for increasing the production of methyl methacrylate, it is necessary not only to increase the methacrolein content of the above-mentioned liquid mixture, but also to lower the water content of the above-mentioned liquid mixture to a level as low as possible.

However, at present, as mentioned above, methacrolein is produced by subjecting at least one starting material selected from the group consisting of isobutylene and tert-butanol to a gas phase catalytic oxidation reaction in the presence of molecular oxygen and in the presence of a catalyst (this reaction is hereinafter frequently referred to simply as a "methacrolein synthesis reaction"). The methacrolein product obtained by the above-mentioned reaction contains a considerable amount of water in addition to by-products. The water contained in the methacrolein product is derived from various sources, such as water generated in the above-mentioned methacrolein synthesis reaction; steam used as a diluent gas; water generated in a dehydration reaction of tert-butanol (when tert-butanol is used as a starting material); and water contained in tert-butanol, which water is derived from an azeotropic tert-butanol/water mixture formed by a specific production process of tert-butanol. Thus, water is inevitably contained in the methacrolein product. Unless the water content of the methacrolein product is lowered by dehydration, it becomes impossible to produce methyl methacrylate efficiently by the direct ML-to-MMA process.

As mentioned above, when the production of methacrolein is conducted by the above-mentioned gas phase catalytic oxidation reaction, methacrolein is generally obtained in the form of gas containing methacrolein and steam. In order to obtain a methacrolein product having a low water content by the gas phase catalytic oxidation reaction, the water content of the above-mentioned gas is lowered, and gaseous methacrolein contained in the gas is separated and recovered in the form of a liquid mixture containing liquid methacrolein. However, in a commercial scale production of methacrolein, a treatment using a known desiccant, such as silica-alumina, zeolite or calcium chloride, cannot be employed as method for lowering the water content of the gas containing methacrolein and steam, because such a known desiccant has a poor dehydrating ability, and an unfavorable polymerization of methacrolein is likely to occur on the surface of the desiccant.

For obtaining the methacrolein product having a low water content by way of lowering the water content of the methacrolein product during the production process for methacrolein, various proposals have been made. For example, Unexamined Japanese Patent Application Laid-Open Specification (Japanese Kokai) No. 49-92007 discloses a method in which gaseous methacrolein in the gas containing gaseous methacrolein and steam is absorbed into an alcohol and the resultant liquid mixture of liquid methacrolein and a liquid alcohol is subjected to an extractive distillation using water as an extraction solvent, to thereby separate and recover methacrolein. However, in this method, since water is used as an extraction solvent, the methacrolein is separated and recovered inevitably in the form of an azeotropic mixture of methacrolein and water [azeotropic point: 63.6° C.; methacrolein/water (weight ratio): 100/7.9]. Therefore, in this method, it is impossible to obtain a methacrolein product having a water content which is lower than that of the azeotropic mixture of methacrolein and water. Further, U.S. Pat. No. 2,514,966 discloses a method in which gaseous methacrolein in the gas containing gaseous methacrolein and steam is absorbed into water. However, in this method, for the same reason as mentioned above in connection with Unexamined Japanese Patent Application Laid-Open Specification No. 49-92007, it is impossible to obtain a methacrolein product having a water content which is lower than that of the azeotropic mixture of methacrolein and water.

Unexamined Japanese Patent Application Laid-Open Specification (Japanese Kokai) No. 55-19213 discloses a method in which an organic compound having a high boiling point, such as an alkylnaphthalene, is used as a solvent, and methacrolein contained in the gas containing methacrolein and steam is absorbed into the solvent to thereby separate and recover methacrolein. However, in this method, during the separation of methacrolein from the mixture of methacrolein and the solvent, the mixture is kept under heated conditions, so that a polymerization of methacrolein is likely to occur, thereby consuming a large amount of methacrolein monomers.

Unexamined Japanese Patent Application Laid-Open Specification (Japanese Kokai) No. 56-87530 (corresponding to U.S. Pat. No. 4,329,513) discloses a method for dehydrating a gas containing an unsaturated aldehyde and steam, which gas is obtained by subjecting at least one starting material selected from the group consisting of propylene, isobutylene and tert-butanol to a gas phase catalytic oxidation reaction. Specifically, the method disclosed in this patent document comprises introducing a gas containing an unsaturated aldehyde and steam, and liquid methanol into a dehydration tower at a lower portion thereof and at an upper portion thereof, respectively, wherein the liquid methanol is introduced in an amount such that substantially all of the methanol can be gasified, thereby allowing the liquid methanol to flow downwardly in the dehydration tower and contact countercurrently with the gas in the dehydration tower, so that the gas is dehydrated to form a dehydrated gas containing the unsaturated aldehyde; and introducing the unsaturated aldehyde-containing dehydrated gas and liquid methanol into an absorption tower, so that the unsaturated aldehyde which is contained in the dehydrated gas is absorbed into the liquid methanol; and recovering the unsaturated aldehyde in the form of a liquid mixture containing the liquid unsaturated aldehyde and the liquid methanol.

However, in this method disclosed in Unexamined Japanese Patent Application Laid-Open Specification No. 56-87530, since methanol is added to each of the gas containing the unsaturated aldehyde (methacrolein) in the dehydration tower and the dehydrated gas containing the unsaturated aldehyde (methacrolein) in the absorption tower, the unsaturated aldehyde is caused to be diluted with methanol, so that the content of the unsaturated aldehyde (methacrolein) in the liquid mixture (containing the liquid unsaturated aldehyde and the liquid methanol) withdrawn from the outlet of the absorption tower is on a level as low as 18 % by weight or less. On the other hand, in the commercial scale production of methyl methacrylate by the direct ML-to-MMA process, as a starting material for the direct ML-to-MMA synthesis reaction, it is preferred to use a methacrolein/methanol liquid mixture having a methacrolein content of not less than 25 % by weight and having a methacrolein/methanol weight ratio of not less than 0.33. That is, the method disclosed in Unexamined Japanese Patent Application Laid-Open Specification No. 56-87530 has a problem in that, although the water content of the methacrolein/methanol liquid mixture can be lowered, it is impossible to increase the methacrolein content of the methacrolein/methanol liquid mixture to a level which is sufficient for improving the productivity of methyl methacrylate in the direct ML-to-MMA process.

With respect to the methacrolein/methanol liquid mixture obtained by the method disclosed in Unexamined Japanese Patent Application Laid-Open Specification No. 56-87530, even if it is attempted to increase the methacrolein content of the methacrolein/methanol liquid mixture by a method in which the methacrolein/methanol liquid mixture withdrawn from the absorption tower is introduced into a distillation tower to thereby concentrate the liquid mixture, it is impossible to obtain a methacrolein/methanol liquid mixture having a satisfactorily high methacrolein content. The reason therefor resides in that, by the above-mentioned method using a distillation tower, only an azeotropic mixture of methacrolein and methanol (azeotropic point: 58.0° C.; methacrolein/methanol weight ratio: 72.2/27.7) is obtained, so that it is impossible to obtain a methacrolein/methanol liquid mixture having a methacrolein content higher than that of the above-mentioned azeotropic mixture. Further, this method is disadvantageous not only in that a distillation tower is additionally needed, but also in that there is a danger that a polymerization of methacrolein occurs in the distillation tower, so that the resultant polymerized product causes troubles in the production system for methyl methacrylate, leading to a difficulty in stable production of methyl methacrylate.

Further, in this Unexamined Japanese Patent Application Laid-Open Specification No. 56-87530, the synthesis of methyl methacrylate by the direct ML-to-MMA process is conducted using an excessive amount of methanol, which is far larger than that consumed in the direct ML-to-MMA synthesis reaction. The reason for the use of an excessive amount of methanol resides in that a considerable amount of methanol is needed in the two preceding steps for dehydrating a gas containing a gaseous methacrolein and steam in a dehydration tower and for absorbing the gaseous methacrolein in an absorption tower. Due to the use of the excessive amount of methanol, it is necessary that a large amount of unreacted methanol be separated from the reaction mixture (containing desired methyl methacrylate) obtained by the direct ML-to-MMA synthesis reaction and that the separated methanol be recycled. Such a separation operation and a recycling operation consume a disadvantageously large amount of energy. On the other hand, it is noted that, when the amount of methanol used in the direct ML-to-MMA process is small, both the conversion of methacrolein and the selectivity for methyl methacrylate in the direct ML-to-MMA process tend to lower.

With respect to the method for separating methanol from the reaction mixture obtained by the direct ML-to-MMA synthesis reaction, and recycling the separated methanol to the dehydration tower and the absorption tower, the following methods have been proposed.

First, as described in Unexamined Japanese Patent Application Laid-Open Specification (Japanese Kokai) No. 58-157740, there is known a method for separating a liquid mixture containing liquid methyl methacrylate and unreacted liquid methanol from a reaction mixture (containing methyl methacrylate, water, methacrolein and methanol) obtained by the direct ML-to-MMA synthesis reaction. Specifically, this method comprises introducing the reaction mixture obtained by the direct ML-to-MMA synthesis reaction into a distillation tower to thereby obtain a liquid mixture containing liquid methyl methacrylate and unreacted liquid methanol from the bottom of the tower, and a liquid mixture containing unreacted liquid methacrolein and unreacted liquid methanol from the top of or an upper portion of the tower. In this method, the methacrolein/methanol liquid mixture obtained from the top of or an upper portion of the tower is recycled to a reactor for the direct ML-to-MMA synthesis reaction.

On the other hand, there is also a known method for separating methanol from the above-mentioned liquid mixture (containing liquid methyl methacrylate and unreacted liquid methanol) obtained by the separation from the reaction mixture produced by the direct ML-to-MMA synthesis reaction. For example, Unexamined Japanese Patent Application Laid-Open Specification (Japanese Kokai) Nos. 57-9739 (corresponding to U.S. Pat. No. 4,518,462) and 57-9740 disclose the following method. The liquid mixture containing liquid methyl methacrylate and unreacted liquid methanol is introduced into a first distillation tower, together with a $C_6$–$C_8$ saturated hydrocarbon, to thereby distill substantially all of the methanol in the form of an azeotropic mixture thereof with the $C_6$–$C_8$ saturated hydrocarbon from the top of the tower. The obtained azeotropic mixture is introduced into a phase separation vessel to thereby separate the mixture into an upper layer composed mainly of $C_6$–$C_8$ saturated hydrocarbon and a lower layer composed mainly of methanol. The obtained $C_6$–$C_8$ saturated hydrocarbon of the upper layer is recycled to the first distillation tower, and the obtained methanol of the lower layer is subjected to a distillation in a second distillation tower, wherein methanol is withdrawn from the bottom of the second distillation tower and recycled to the dehydration tower and the absorption tower. From the top of the second distillation tower, the $C_6$–$C_8$ saturated hydrocarbon is distilled in the form of an azeotropic mixture thereof with methanol, which is recycled to the phase separation vessel.

However, when this method of Unexamined Japanese Patent Application Laid-Open Specification Nos. 57-9739 and 57-9740 is combined with the method of Unexamined Japanese Patent Application Laid-Open Specification No. 58-157740 so as to conduct a continuous production of methyl methacrylate, the production process becomes disadvantageously complicated and extensive, because this process needs not only a phase separation operation and distillation operations using three distillation towers, but also includes a plurality of recycling steps.

Further, the above method is disadvantageous in that, when the liquid mixture containing a $C_6$-$C_8$ saturated hydrocarbon, liquid methyl methacrylate and liquid methanol is introduced into the first distillation tower, it is necessary to control the amount of the saturated hydrocarbon present in the tower, the amount of the liquid mixture to be introduced, the operation temperature of the distillation tower, the thermal input for heating and the amounts of products withdrawn from the top and bottom of the tower so that substantially all of the introduced saturated hydrocarbon is maintained at a position higher than a plate at which the liquid mixture is introduced into the tower. When a part or all of the saturated hydrocarbon is present at a position lower than a plate at which the liquid mixture is introduced into the tower, the water contained in the liquid mixture introduced into the first distillation tower disadvantageously undergoes azeotropy with the saturated hydrocarbon and, hence, the water enters the separated and recovered methanol, so that the water content of the separated and recovered methanol exceeds 3% by weight. When the methanol having such a high water content is introduced into the dehydration tower and the absorption tower, the water content of a liquid mixture (containing liquid methacrolein and liquid methanol) obtained from the absorption tower is increased, rendering the liquid mixture unsuitable for use as a feedstock for the direct ML-to-MMA synthesis reaction.

In addition, the above method has also the following disadvantage. When the operation conditions of the first distillation tower are changed or when the operation of the first distillation tower is started or stopped, the operation conditions of the tower become unsteady, thus causing the above-mentioned saturated hydrocarbon in the introduced liquid mixture to flow down inside the tower toward the bottom thereof through a plurality of plate regions of the tower. Since the saturated hydrocarbon is a poor solvent for the produced polymers and the by-produced polymers present in the introduced liquid mixture, a deposition of these polymers occurs, leading to a clogging of the plates and pipes of the first distillation tower. Frequently, this clogging is so serious as to make it impossible to continue the operation of the first distillation tower.

Moreover, the above method has a further problem in that a plurality of azeotropic systems having azeotropic points close to each other are disadvantageously formed in a distillation tower which is used for separating methanol from a reaction mixture (containing methyl methacrylate, water, methacrolein and methanol) obtained by the direct ML-to-MMA synthesis reaction, wherein the resultant separated methanol is intended to be used for dehydrating a gas containing methacrolein gas and steam and for absorbing methacrolein gas. Due to the formation of such plurality of azeotropic systems, it becomes difficult to stably operate such distillation tower. In one example, a plurality of azeotropic systems are formed in the distillation tower used for separating and obtaining a liquid mixture containing unreacted liquid methacrolein and unreacted liquid methanol from the above-mentioned reaction mixture obtained by the direct ML-to-MMA synthesis reaction, which distillation tower is described in Unexamined Japanese Patent Application Laid-Open Specification (Japanese Kokai) No. 58-157740. In another example, a plurality of azeotropic systems are also formed in the first and second distillation towers used in the method of Unexamined Japanese Patent Application Laid-Open Specification (Japanese Kokai) Nos. 57-9739 and 57-9740. More specifically, the below-mentioned azeotropic systems are formed in the above-mentioned distillation tower used (for separating and obtaining a liquid mixture containing unreacted liquid methacrolein and unreacted liquid methanol) in the method of Unexamined Japanese Patent Application Laid-Open Specification (Japanese Kokai) No. 58-157740 (the temperatures in parentheses show azeotropic points).

methanol/acetone (55.5° C.),
mathacrolein/methanol (58.0° C.),
water/methacrolein (63.6° C.),
methyl methacrylate/methanol (64.5° C.),
methyl methacrylate/water (83.0° C.), and
methacrylic acid/water (99.3° C.).

Further, when n-hexane is used as the saturated hydrocarbon in the method of Unexamined Japanese Patent Application Laid-Open Specification (Japanese Kokai) Nos. 57-9739 and 57-9740, the below-mentioned azeotropic systems are formed between the main components of the liquid mixture in the first distillation tower (the temperatures in parentheses show azeotropic points).

n-hexane/methanol (49.9° C.),
water/n-hexane (61.6° C.),
methyl methacrylate/methanol (64.5° C.),
methyl methacrylate/water (83.0° C.), and
methacrylic acid/water (99.3° C.).

In addition, in the method of Unexamined Japanese Patent Application Laid-Open Specification (Japanese Kokai) Nos. 57-9739 and 57-9740, the below-mentioned azeotropic systems are formed between the main components of the above-mentioned upper methanol layer in the second distillation tower (the temperatures in parentheses show azeotropic points).

n-hexane/methanol (49.9° C.), and
water/n-hexane (61.6° C.).

Also, it is possible that the below-mentioned azeotropic systems are formed between trace substances (such as by-products) in each of the above-mentioned distillation towers (the temperatures in parentheses show azeotropic points).

mathacrolein/n-hexane (56.1° C.),
water/isobutylaldehyde (64.3° C.),
methanol/isobutylaldehyde (62.7° C.),
water/methacrolein (63.6° C.),
methyl isobutyrate/methanol (64.0° C.), and
water/methyl isobutyrate (77.7° C.).

Therefore, due to the formation of these azeotropic systems, when the conditions in the distillation tower are caused to change, e.g. when the internal temperature of the distillation tower changes by several centigrades, the composition of the distillate changes, so that it becomes difficult to stably operate the distillation tower. Further, trace substances, such as by-products, enter and are accumulated in the recycled system by azeotropy between the main components of the distillate, so that the composition of the distillate is caused to change, leading to an increased difficulty in stable operation of the distillation tower. For example, in the method of Unexamined Japanese Patent Application Laid-Open Specification (Japanese Kokai) Nos. 57-9739 and 57-9740, when a trace amount of methacrolein in the first distillation tower undergoes azeotropy with n-hexane and the resultant azeotropic mixture enters the subsequent separation vessel, problems arise not only in that the compositions of the upper layer liquid and the lower layer liquid obtained in the separation vessel are likely to change, but also in that the methacrolein accumulates in the separation vessel, so that the change in the compositions of the upper layer liquid and the lower layer liquid is amplified with the lapse of the operation time, rendering it very difficult to stably operate the distillation tower.

As is apparent from the above, in the conventional methods in which separated methanol is used for dehydrating a gas containing methacrolein gas and steam and for absorbing methacrolein gas in order to obtain a liquid mixture (containing liquid methacrolein and liquid methanol) which has a high methacrolein content and a low water content and hence is suitable for use as a feedstock for the direct ML-to-MMA synthesis reaction, problems arise not only in that a large amount of methanol is necessary, but also in that the production process for methyl methacrylate becomes complicated and extensive, and the stable operation of a production plant for methyl methacrylate becomes difficult. Thus, it has conventionally been difficult to commercially carry out the direct ML-to-MMA process.

SUMMARY OF THE INVENTION

In this situation, with respect to a method which comprises: treating gas (a) containing methacrolein gas and steam by using a dehydration tower, followed by a treatment by using an absorption tower, to thereby prepare a methacrolein/methanol liquid mixture having a low water content; and introducing the methacrolein/methanol liquid mixture into an oxidative esterification reactor to thereby perform the direct ML-to-MMA synthesis reaction, the present inventors have made extensive and intensive studies with a view toward developing an improvement in which a methacrolein/methanol liquid mixture having not only a low water content but also a high methacrolein content can be obtained, so that the desired methyl methacrylate can be produced with high efficiency and high stability. As a result, it has unexpectedly been found that, by using a method comprising: introducing the above-mentioned gas (a) and a liquid mixture (I) containing liquid methacrolein and liquid methanol into a dehydration tower at a lower portion thereof and at an upper portion thereof, respectively, thereby allowing the liquid mixture (I) to flow downwardly and contact countercurrently with the gas (a), to thereby obtain a dehydrated gas mixture (b) containing methacrolein gas and methanol gas; and introducing the dehydrated gas mixture (b) and a liquid mixture (II) containing liquid methacrolein and liquid methanol into an absorption tower at a lower portion thereof and at an upper portion thereof, respectively, so that the methacrolein gas and methanol gas which are contained in the dehydrated gas mixture (b) is absorbed by the liquid mixture (II), it becomes possible to provide a methacrolein/methanol liquid mixture (III) which has not only a low water content but also a high methacrolein content, and that, therefore, by introducing the liquid mixture (III) into a reactor to perform the direct ML-to-MMA synthesis reaction, methyl methacrylate can be produced in high efficiency. Further, it has also unexpectedly been found that, by recycling a liquid mixture (IV) containing liquid methacrolein and liquid methanol (which is separated from the reaction mixture obtained by the direct ML-to-MMA synthesis reaction) as the liquid mixtures (I) and/or (II), the production of methyl methacrylate can be performed without using apparatuses for the separation of and recycling of methanol alone, which are necessarily used in the conventional methods. This is advantageous in that the improved production method is free from the troubles caused by the use of the above-mentioned apparatuses for the separation of and recycling of methanol alone, so that the desired methyl methacrylate can be produced stably. The present invention has been made, based on these novel findings.

Accordingly, it is a primary object of the present invention to provide a method for producing methyl methacrylate, which can provide a methacrolein/methanol liquid mixture for the direct ML-to-MMA synthesis reaction, which liquid mixture has not only a low water content but also a high methacrolein content, and which, therefore, can be advantageously used for the direct ML-to-MMA synthesis reaction, so that the desired methyl methacrylate can be produced stably and in high efficiency.

The foregoing objects, features and advantages of the present invention will be apparent from the following detailed description and appended claims taken in connection with the accompanying drawings.

DESCRIPTION OF REFERENCE NUMERALS

Figure 1:
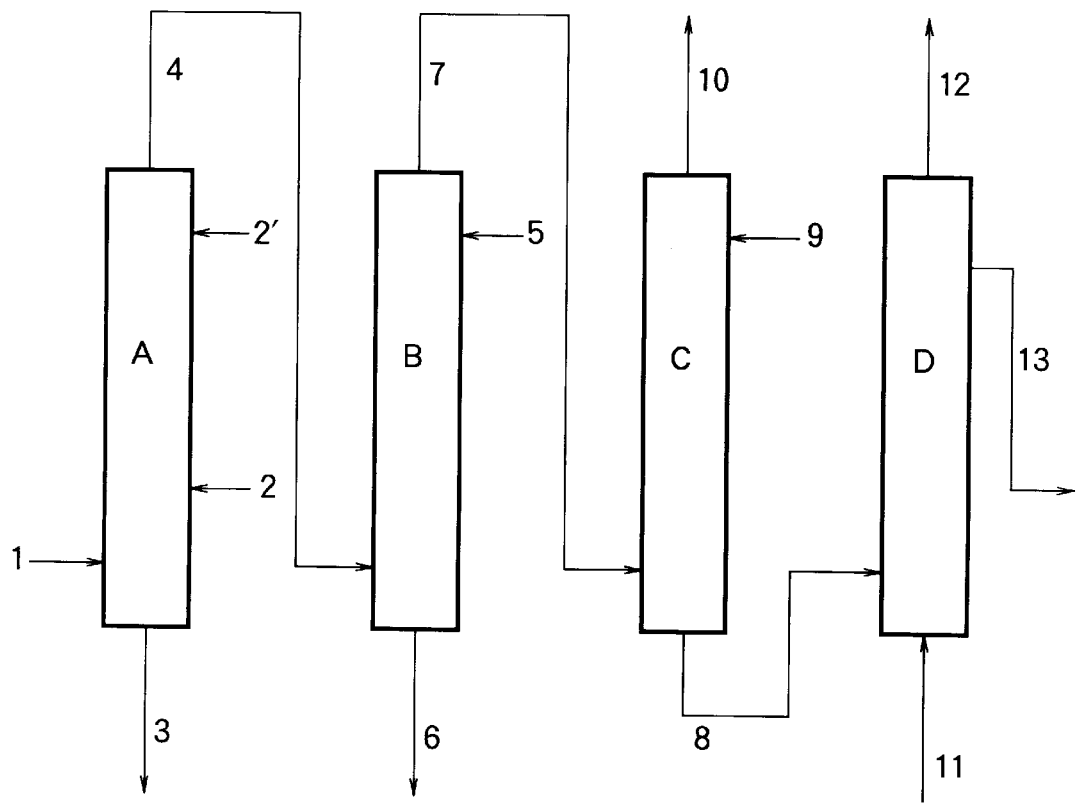
FIG. 1 is a diagram showing an example of a system for practicing the method of the present invention.

A Quenching tower
B Dehydration tower
C Absorption tower
D Direct ML-to-MMA synthesis reactor
E Unreacted methacrolein separation tower
F Unreacted methanol separation tower
G Phase separation vessel
H Unreacted methanol recovering tower
J Separation tower for separating a liquid mixture containing liquid methacrolein and liquid methanol from a reaction mixture obtained by the direct ML-to-MMA synthesis reaction
1 Gas [gas (a)] containing methacrolein and steam
2,2' Quenching water
3 Waste water
4 Partially dehydrated gas containing methacrolein and steam, which has been cooled and partially dehydrated in quenching tower A
5 Liquid mixture (I) containing liquid methacrolein and liquid methanol [which may be a liquid mixture (IV) (containing liquid methacrolein and liquid methanol) obtained by separation from a reaction mixture obtained by the direct ML-to-MMA synthesis reaction]
6 Separated water
7 Dehydrated gas mixture (b) containing methacrolein gas and methanol gas
8 Liquid mixture (III) containing liquid methacrolein and liquid methanol (which is subjected to the direct ML-to-MMA synthesis reaction)
9 Liquid mixture (II) containing liquid methacrolein and liquid methanol [which may be a liquid mixture (IV) (containing liquid methacrolein and liquid methanol) obtained by separation from a reaction mixture obtained by the direct ML-to-MMA synthesis reaction]
10 Vent-gas
11 Molecular oxygen (which may be molecular oxygen itself or a molecular oxygen-containing gas)
12 Vent-gas
13 Reaction mixture obtained by the direct ML-to-MMA synthesis reaction
14 Liquid mixture containing liquid methyl methacrylate and liquid methanol
15 Low boiling point by-products
16 Liquid mixture containing recovered liquid methacrolein and liquid methanol
17 Crude methyl methacrylate
18 Azeotropic mixture of methanol and a $C_6$–$C_8$ saturated hydrocarbon
19 $C_6$–$C_8$ saturated hydrocarbon
20 Recycled liquid composed mainly of $C_6$–$C_8$ saturated hydrocarbon, which is the upper layer in phase separation vessel G
21 Liquid composed mainly of methanol, which is the lower layer in phase separation vessel G
22 Recovered methanol
23 Azeotropic mixture of methanol and a $C_6$-$C_8$ saturated hydrocarbon
24 Liquid mixture containing liquid methyl methacrylate and water
25 Liquid mixture (IV) containing liquid methacrolein and liquid methanol Detailed Description of the Invention According to the present invention, there is provided a method for producing methyl methacrylate, which comprises:

(1) subjecting at least one starting material selected from the group consisting of isobutylene and tert-butanol to a gas phase catalytic oxidation reaction with molecular oxygen in the presence of a catalyst to thereby obtain gas (a) containing methacrolein gas and steam;

(2) introducing the gas (a) and a liquid mixture (I) containing liquid methacrolein and liquid methanol into a dehydration tower at a lower portion thereof and at an upper portion thereof, respectively, thereby allowing the liquid mixture (I) to flow downwardly in the dehydration tower and contact countercurrently with the gas (a) in the dehydration tower, so that the liquid mixture (I) is gasified to thereby generate a gas mixture (I') containing methacrolein gas and methanol gas while causing the steam contained in the gas (a) to be condensed to thereby produce water, wherein the produced water is discharged from a bottom portion of the dehydration tower to thereby dehydrate the gas (a), while withdrawing the resultant dehydrated gas (a') containing the methacrolein gas, together with the gas mixture (I'), from an uppermost portion of the dehydration tower in the form of a dehydrated gas mixture (b) containing methacrolein gas and methanol gas;

(3) introducing the dehydrated gas mixture (b) and a liquid mixture (II) containing liquid methacrolein and liquid methanol into an absorption tower at a lower portion thereof and at an upper portion thereof, respectively, thereby allowing the liquid mixture (II) to flow downwardly and contact countercurrently with the dehydrated gas mixture (b) in the absorption tower, wherein the liquid mixture (II) is introduced in an amount sufficient to absorb substantially all of the methacrolein gas and methanol gas which are contained in the dehydrated gas mixture (b), thus causing substantially all of the methacrolein gas and methanol gas of the dehydrated gas mixture (b) to be absorbed into the liquid mixture (II), to thereby obtain a liquid mixture (III) containing liquid methacrolein and liquid methanol, followed by withdrawal of the liquid mixture (III) from a bottom portion of the absorption tower; and (4) introducing the withdrawn liquid mixture (III) into an oxidative esterification reactor and subjecting the methacrolein and methanol, which are contained in the liquid mixture (III), to an oxidative esterification reaction in the reactor in the presence of molecular oxygen and in the presence of a palladium catalyst, to thereby produce methyl methacrylate in the form of a reaction mixture containing methyl methacrylate, water, methacrolein and methanol.

For easy understanding of the present invention, the essential features and various embodiments of the present invention is enumerated below.

1. A method for producing methyl methacrylate, which comprises:

(1) subjecting at least one starting material selected from the group consisting of isobutylene and tert-butanol to a gas phase catalytic oxidation reaction with molecular oxygen in the presence of a catalyst to thereby obtain gas (a) containing methacrolein gas and steam;

(2) introducing the gas (a) and a liquid mixture (I) containing liquid methacrolein and liquid methanol into a dehydration tower at a lower portion thereof and at an upper portion thereof, respectively, thereby allowing the liquid mixture (I) to flow downwardly in the dehydration tower and contact countercurrently with the gas (a) in the dehydration tower, so that the liquid mixture (I) is gasified to thereby generate a gas mixture (I') containing methacrolein gas and methanol gas while causing the steam contained in the gas (a) to be condensed to thereby produce water, wherein the produced water is discharged from a bottom portion of the dehydration tower to thereby dehydrate the gas (a), while withdrawing the resultant dehydrated gas (a') containing the methacrolein gas, together with the gas mixture (I'), from an uppermost portion of the dehydration tower in the form of a dehydrated gas mixture (b) containing methacrolein gas and methanol gas;

(3) introducing the dehydrated gas mixture (b) and a liquid mixture (II) containing liquid methacrolein and liquid methanol into an absorption tower at a lower portion thereof and at an upper portion thereof, respectively, thereby allowing the liquid mixture (II) to flow downwardly and contact countercurrently with the dehydrated gas mixture (b) in the absorption tower, wherein the liquid mixture (II) is introduced in an amount sufficient to absorb substantially all of the methacrolein gas and methanol gas which are contained in the dehydrated gas mixture (b), thus causing substantially all of the methacrolein gas and methanol gas of the dehydrated gas mixture (b) to be absorbed into the liquid mixture (II), to thereby obtain a liquid mixture (III) containing liquid methacrolein and liquid methanol, followed by withdrawal of the liquid mixture (III) from a bottom portion of the absorption tower; and (4) introducing the withdrawn liquid mixture (III) into an oxidative esterification reactor and subjecting the methacrolein and methanol, which are contained in the liquid mixture (III), to an oxidative esterification reaction in the reactor in the presence of molecular oxygen and in the presence of a palladium catalyst, to thereby produce methyl methacrylate in the form of a reaction mixture containing methyl methacrylate, water, methacrolein and methanol.

2. The method according to item 1 above, wherein at least one liquid mixture selected from the group consisting of the liquid mixtures (I) and (II) is a liquid mixture (IV) containing liquid methacrolein and liquid methanol, wherein the liquid mixture (IV) is obtained by separation from the reaction mixture obtained by the oxidative esterification reaction.

3. The method according to item 1 or 2 above, wherein the contact of the liquid mixture (I) with the gas (a) in the dehydration tower is conducted at a temperature of from 10 to 60° C. under a pressure of from 0.2 to 3.0 kg/cm².

4. The method according to any one of items 1 to 3 above, wherein the contact of the liquid mixture (II) with the dehydrated gas mixture (b) in the absorption tower is conducted at a temperature of from −25 to 10° C. under a pressure of from 0.2 to 3.0 kg/cm².

5. The method according to any one of items 1 to 4 above, wherein the liquid mixture (I) is introduced into the dehydration tower in an amount of from 10 to 500 g per Nm³ (wherein the Nm³ means m³ as measured under the normal conditions, i.e., at 0° C. under 1 atm.) of the gas (a).

6. The method according to any one of items 1 to 5 above, wherein the liquid mixture (II) is introduced into the absorption tower in an amount of from 50 to 1000 g per Nm³ (wherein the Nm³ means m³ as measured under the normal conditions, i.e., at 0° C. under 1 atm.) of the dehydrated gas mixture (b).

7. The method according to any one of items 1 to 6 above, wherein each of the liquid mixtures (I) and (II) independently contains liquid methacrolein and liquid methanol in amounts of 5 to 60% by weight and 40 to 95% by weight, respectively, based on the respective weight of the liquid mixtures (I) and (II).

8. The method according to any one of items 2 to 7 above, wherein the liquid mixture (IV) further contains methyl methacrylate in an amount not exceeding 25% by weight, based on the weight of the liquid mixture (IV).

9. The method according to any one of items 1 to 8 above, wherein the content of the liquid methacrolein in the liquid mixture (III) is from 25 to 69% by weight, based on the weight of the liquid mixture (III), and the weight ratio of the liquid methacrolein to the liquid methanol in the liquid mixture (III) is 0.33 to 2.2.

Hereinbelow, the present invention will be described in detail.

The definitions of the liquid mixtures (I), (II), (III) and (IV) are given below.

Liquid mixture (I): a liquid mixture containing liquid methacrolein and liquid methanol, which, in the method of the present invention, is introduced into a dehydration tower at an upper portion thereof for dehydrating gas (a) containing methacrolein and steam. This liquid mixture (I) may be the below-mentioned liquid mixture (IV).

Liquid mixture (II): a liquid mixture containing liquid methacrolein and liquid methanol, which, in the method of the present invention, is introduced into an absorption tower at an upper portion thereof for absorbing the methacrolein gas and methanol gas which are contained in dehydrated gas mixture (b) containing methacrolein gas and methanol gas. This liquid mixture (II) may be the below-mentioned liquid mixture (IV).

Liquid mixture (III): a liquid mixture containing liquid methacrolein and liquid methanol, which, in the method of the present invention, is obtained by allowing the above-mentioned liquid mixture (II) (containing liquid methacrolein and liquid methanol) to absorb the methacrolein gas and methanol gas which are contained in dehydrated gas mixture (b) in the absorption tower, wherein this liquid mixture (III) is withdrawn from the bottom portion of the absorption tower, and then, used as a feedstock for the above-mentioned oxidative esterification reaction (the direct ML-to-MMA synthesis reaction).

Liquid mixture (IV): a liquid mixture containing liquid methacrolein and liquid methanol, which, in the method of the present invention, is obtained by separation from a reaction mixture (containing methyl methacrylate, water, methacrolein and methanol) produced by the above-mentioned oxidative esterification reaction (the direct ML-to-MMA synthesis reaction). This liquid mixture (IV) can be recycled and introduced into the dehydration tower at an upper portion thereof as the above-mentioned liquid mixture (I) and/or into the absorption tower at an upper portion thereof as the above-mentioned liquid mixture (II).

In the method of the present invention, first, at least one starting material selected from the group consisting of isobutylene and tert-butanol is subjected to a gas phase catalytic oxidation reaction with molecular oxygen in the presence of a catalyst to thereby obtain gas (a) containing methacrolein gas and steam. With respect to the illustrative method for preparing gas (a), an appropriate method may be chosen from various conventional methods.

Next, the obtained gas (a) and liquid mixture (I) containing liquid methacrolein and liquid methanol are introduced into a dehydration tower at a lower portion thereof and at an upper portion thereof, respectively, thereby allowing liquid mixture (I) to flow downwardly in the dehydration tower and contact countercurrently with the gas (a) in the dehydration tower, so that the liquid mixture (I) is gasified to thereby generate a gas mixture (I') containing methacrolein gas and methanol gas. When the above gasification occurs, the steam contained in the gas (a) is deprived of the latent heat of vaporization, so that the steam is condensed and separated from the gas (a). The resultant water flows downwardly in the dehydration tower and is withdrawn from the bottom of the dehydration tower as a separated water. As a result, the gas (a) is dehydrated to thereby obtain a dehydrated gas (a') containing the methacrolein gas, which is withdrawn together with the gas mixture (I') from an uppermost portion of the dehydration tower in the form of a dehydrated gas mixture (b) containing methacrolein gas and methanol gas.

There is no limitation with respect to the type of dehydration tower used in the method of the present invention, and any conventional distillation tower, such as a plate tower or a packed tower, can be used. However, since methacrolein, which is introduced into the dehydration tower, is an easily polymerizable compound, it is preferred to use a tower having a structure such that the clogging with the polymerized products does not occur or a structure such that, even when the clogging with the polymerized products occurs, the polymerized products can be easily removed. Specific examples of dehydration towers include a plate tower provided with a sieve tray, a cascade tray, a turbogrid tray, a ripple tray or the like, and a packed tower which is regularly packed with packing materials, such as Mellapak and Sulzer packing (each manufactured and sold by Sumitomo Heavy Industries, Ltd., Japan).

In the method of the present invention, it is preferred that the contact of the liquid mixture (I) with the gas (a) in the dehydration tower is conducted at a temperature of from 10 to 60° C., more advantageously from 10 to 40° C., under a pressure of from 0.2 to 3.0 kg/cm$^2$, more advantageously from 0.5 to 2.0 kg/cm$^2$. When the contact of the liquid mixture (I) with the gas (a) is conducted under the above-mentioned conditions, there can be obtained a methacrolein/methanol-containing dehydrated gas (b) having methacrolein in high ratio (1.0 to 4.9 in terms of the methacrolein/methanol weight ratio). When the contact of the liquid mixture (I) with the gas (a) in the dehydration tower is conducted at a temperature exceeding 60° C. and/or under a pressure exceeding 3.0 kg/cm$^2$, the dehydration can be conducted using a dehydration tower having a small size; however, the unfavorable polymerization of methacrolein occurs due to the high temperature in the dehydration tower, thereby causing disadvantageous phenomena such that a considerable amount of the methacrolein is consumed in the polymerization, and that the production equipment is clogged with the polymerized product.

In the method of the present invention, a reactor used for the methacrolein synthesis reaction and the dehydration tower may be connected to each other by a pipeline so that the gas (a) obtained in the reactor can be directly and continuously introduced into a lower portion of the dehydration tower. When the gas (a) obtained in the reactor is directly and continuously introduced into the dehydration tower, it is preferred that the countercurrent contact in the dehydration tower is performed under a pressure of 3.0 kg/cm$^2$ or less. In this case, when the pressure for performing the countercurrent contact in the dehydration tower exceeds 3.0 kg/cm$^2$, the selectivity for methacrolein in the methacrolein synthesis reaction is likely to lower.

On the other hand, when the contact of the liquid mixture (I) with the gas (a) in the dehydration tower is conducted at a temperature of less than 10° C. and/or under a pressure of less than 0.2 kg/cm$^2$, the occurrence of the polymerization of the methacrolein is suppressed, so that the methacrolein content of the gas (b) becomes high; however, it becomes necessary to use a dehydration tower having a disadvantageously large size, thereby increasing the load of a cooling apparatus used for lowering the temperature of the dehydration tower.

In the method of the present invention, it is preferred that the contents of the liquid methacrolein and the liquid methanol in the liquid mixture (I) are 5 to 60% by weight and 40 to 95% by weight, respectively, more advantageously, 10 to 50% by weight and 40 to 75% by weight, respectively, based on the weight of the liquid mixture (I). In the method of the present invention, as the liquid mixture (I) which is introduced into the dehydration tower, use can be made of a liquid mixture (IV) containing liquid methacrolein and liquid methanol, which liquid mixture (IV) is obtained by separation from the reaction mixture (containing methyl methacrylate, water, methacrolein and methanol) obtained by the direct ML-to-MMA synthesis reaction, that is, the liquid mixture (IV) may be recycled to the dehydration tower as the liquid mixture (I).

Figure 3:
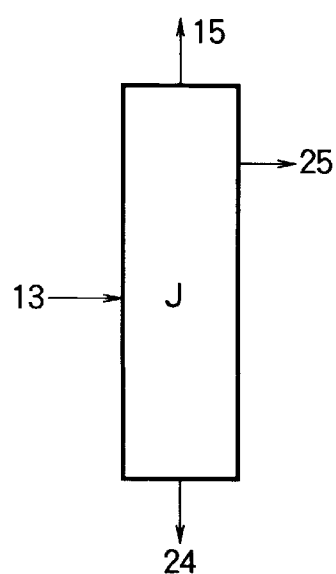
FIG. 3 is a diagram showing an example of a separation tower usable in the method of the present invention for separating methacrolein and methanol from the reaction mixture obtained by the direct ML-to-MMA synthesis reaction to thereby obtain a liquid mixture (IV).

In the method of the present invention, it is preferred that the water content of the liquid mixture (I) is as low as possible. Specifically, it is preferred that the water content of the liquid mixture (I) is 0.5% by weight or less, more advantageously 0.2% by weight or less. When the liquid mixture (IV) is used as the liquid mixture (I), the water content of liquid mixture (IV) can be adjusted to a level within the above-mentioned range by a method in which a reaction mixture (containing methyl methacrylate, water, methacrolein and methanol) obtained by the direct ML-to-MMA synthesis reaction is introduced into a distillation tower (as shown in FIG. 3 annexed hereto and described below), and subjected to a conventional distillation operation.

Further, the liquid mixture (I) may contain compounds other than methacrolein and methanol as long as the compounds do not adversely affect the direct ML-to-MMA synthesis reaction. For example, the liquid mixture (IV) generally contains small amounts of by-products formed in the methacrolein synthesis reaction. With respect to the liquid mixture (IV), which may be introduced into the dehydration tower as the liquid mixture (I), the liquid mixture (IV) generally contains (in addition to the above-mentioned by-products of the methacrolein synthesis reaction) 1 to 25% by weight of methyl methacrylate and small amounts of by-products formed in the direct ML-to-MMA synthesis reaction. Representative examples of by-products which are contained in each of the liquid mixtures (I) and (IV) include acetone, methyl formate, methyl acetate and methyl acrylate. The presence of these by-products in the liquid mixtures (I) and (IV) only slightly lowers the contents of methacrolein and methanol contained in the liquid mixture (III) which is subjected to the direct ML-to-MMA synthesis reaction, and does not adversely affect the direct ML-to-MMA synthesis reaction.

In the method of the present invention, for suppressing the polymerization of methacrolein (which is an easily polymerizable compound) contained in the liquid mixture (I) to thereby prevent the polymerized product from clogging and fouling the heat exchangers, pipes and the like, a polymerization inhibitor, such as hydroquinone, may be added to a liquid phase in the dehydration tower. In this case, it is preferred that the concentration of the polymerization inhibitor in the liquid phase is in the range of from 10 ppm by weight to 1% by weight. The polymerization inhibitor may be independently introduced into the dehydration tower at an upper portion thereof. Alternatively, an appropriate amount of the polymerization inhibitor may be added to the liquid mixture (I), and introduced into the dehydration tower together with the liquid mixture (I).

In the method of the present invention, the amount of the liquid mixture (I) to be introduced into the dehydration tower varies depending on the dehydration conditions in the dehydration tower in which the contact of the liquid mixture (I) with the gas (a) is conducted [such as the temperature and pressure in the dehydration tower, the water content of the gas (a), and the amount of the gas (a) introduced into the dehydration tower]. However, it is preferred that the amount of the liquid mixture (I) introduced to the dehydration tower be such that substantially all of the liquid mixture (I) introduced can be gasified. For this purpose, it is preferred that the amount of the liquid mixture (I) is from 10 to 500 g, more advantageously from 30 to 200 g, per 1 $Nm^3$ of the gas (a), wherein $Nm^3$ means $m^3$ as measured under the normal conditions, i.e., at 0° C. under 1 atm. When the amount of the liquid mixture (I) is maintained at a level within the above-mentioned range, it is possible to obtain, from an uppermost portion of the dehydration tower, the dehydrated gas mixture (b) containing water in a low ratio (as low as 0.001 to 0.003 in terms of the water/methacrolein weight ratio) and containing methacrolein in a high ratio (as high as 1.0 to 4.9 in terms of the methacrolein/methanol weight ratio). When the amount of the liquid mixture (I) exceeds 500 g per 1 $Nm^3$ of the gas (a), the water content of the dehydrated gas mixture (b) lowers; however, disadvantages are likely to be caused such that a part of each of the methacrolein and the methanol, which are contained in the liquid mixture (I), flows down to the bottom of the dehydration tower and is withdrawn from the bottom of the dehydration tower, together with the separated water, thereby necessitating an operation for recovering the methacrolein and methanol from the separated water. On the other hand, when the amount of the liquid mixture (I) is less than 10 g per 1 $Nm^3$ of the gas (a), the water content of the dehydrated gas mixture (b) is likely to become disadvantageously high.

Further, in the method of the present invention, it is preferred that the gas (a) containing methacrolein and steam is indirectly and/or directly cooled prior to the introduction of the gas (a) into the dehydration tower. In this case, it is preferred that the gas (a) is cooled to a temperature of from 30 to 60° C., more advantageously from 40 to 50° C., as measured with respect to the gas (a) having a pressure of 1.0 kg/cm2). Although the gas (a) contains high boiling point by-products in addition to methacrolein and steam, the cooling of the gas (a) easily prevents the high boiling by-products and most of the steam from being introduced into the dehydration tower. When the gas (a) is directly introduced into the dehydration tower without being cooled prior to the introduction and contacted countercurrently with the liquid mixture (I), a large amount of the liquid mixture (I) is needed for dehydrating the gas (a), so that the methacrolein content of the liquid mixture (III) (which is subjected to the direct ML-to-MMA synthesis reaction) containing liquid methacrolein and liquid methanol lowers.

An illustrative example of a method for quenching the gas (a) is described below. The gas (a) is introduced into a quenching tower (which has two quenching water inlets at an upper portion thereof and at a lower portion thereof) at a bottom portion thereof and contacted with a quenching water supplied into the quenching tower at the lower portion thereof, thereby quenching the gas (a). Most of the steam contained in the gas (a) is condensed into water, and then the condensate water flows down to a bottom portion of the quenching tower. The condensate water is discharged from the bottom portion of the quenching tower to the outside of the quenching system. High boiling point by-products (examples of high boiling point by-products include water-soluble organic acid, such as methacrylic acid, acrylic acid, acetic acid, maleic acid which are by-produced by the methacrolein synthesis reaction; and furfural and terephthalic acid and the like which are produced by cyclodimerization of the by-produced organic acids or the synthesized methacrolein) are also discharged from the bottom portion of the quenching tower to the outside of the quenching system, together with the condensate water. The water produced can be recycled as a quenching water after it is cooled in a cooling heat-exchanger, or the like. However, the high boiling point by-products contained in the water causes fouling of the internal cooling portion of the heat exchanger. In an extreme case, the heat exchanger is clogged with the high boiling point products. For preventing the clogging of the heat exchanger, for example, in the case of recycling the water produced by condensation as quenching water, it is preferred that the supply of quenching water to the quenching tower is conducted separately at an upper portion thereof and at a lower portion thereof, and the condensate water which is withdrawn from the bottom of the quenching tower and recycled is supplied only to the lower portion of the quenching tower, while supplying to the upper portion of the quenching tower the condensate water withdrawn from the middle portion of the quenching tower and/or supplying quenching water from other sources. For operating the heat exchanger continuously for commercial practice, it is preferred to use flushing water or the like so as to reduce a sticking of deposition and remove stuck substances. For conducting the operation easily, it is preferred that the bottom portion of the quenching tower is designed so as to have a empty structure or a vessel structure without a plate and a packing, for improving the efficiency of gas-liquid contact. In this case, the gas-liquid contact is conducted by directly spraying the quenching water (introduced into a quenching tower at the lower portion thereof) to the gas (a). Further, it is preferred that the water withdrawn from a bottom portion of the above-mentioned dehydration tower is employed as quenching water and that methanol, methacrolein and methyl methacrylate, which are contained in the water in small quantities, are gasified into the gas (a) to thereby decreasing the loss of these materials.

In the step of quenching conducted at the bottom portion of the quenching tower, the gas (a) is rapidly quenched to a temperature preferably of from room temperature to 95° C., more preferably from 30 to 80° C., so that the gas (a) is partially dehydrated. When the temperature is higher than 95° C., polymerization of the methacrolein occurs. On the other hand, when the temperature is lower than room temperature, high boiling point by-products, such as terephthalic acid, are likely to deposit on the inner wall surfaces of the bottom portion of the quenching tower and the pipes.

The quenched, partially dehydrated gas (a) ascends toward the uppermost portion of the quenching tower, and, during the ascending, the gas (a) contacts countercurrently with the quenching water. The gas (a) is further quenched so that the temperature of the uppermost portion of the quenching tower becomes preferably from 30 to 60° C., more preferably from 40 to 50° C. under a pressure of 1.0 kg/cm$^2$. The gas (a) is then withdrawn from the uppermost portion of the quenching tower, and introduced into the dehydration tower at a lower portion thereof.

There is no limitation on the type of the quenching tower at its region in which the partially dehydrated gas (a) contacts countercurrently with the quenching water, and any type of the conventional distillation tower, such as a plate tower or a packed tower, can be used. However, since methacrolein, which is introduced into the quenching tower, is an easily polymerizable compound, and deposition of the polymerized methacrolein and other high boiling point by-products (such as terephthalic acid) is likely to occur, it is preferred to use a tower having a structure such that the clogging with the polymerized products and other deposits does not occur or having a structure such that, even when the clogging with the polymerized products and other deposits occurs, the polymerized products and other deposits can be easily removed. Specific examples of quenching towers include a plate tower provided with a sieve tray, a cascade tray, a turbogrid tray, a ripple tray or the like, and a packed tower which is regularly packed with packing materials, such as Mellapak and Sulzer packing (each manufactured and sold by Sumitomo Heavy Industries, Ltd., Japan).

As described above, the gas (a), if desired, is quenched in the quenching tower, and then dehydrated in the dehydration tower, to thereby obtain a dehydrated gas mixture (b) containing methacrolein gas and methanol gas.

Moreover, it should be noted that one tower is workable as a quenching tower and as a dehydration tower at a lower portion thereof and at a upper portion thereof, respectively.

The dehydrated gas mixture (b) (containing methacrolein gas and methanol gas) withdrawn from the uppermost portion of the dehydration tower, and a liquid mixture (II) containing liquid methacrolein and liquid methanol are introduced into an absorption tower at a lower portion thereof and at an upper portion thereof, respectively, thereby allowing said liquid mixture (II) to flow downwardly and contact countercurrently with the dehydrated gas mixture (b) in said absorption tower, wherein the liquid mixture (II) is introduced in an amount sufficient to absorb substantially all of the methacrolein gas and methanol gas which are contained in the dehydrated gas mixture (b), to thereby obtain a liquid mixture (III) containing liquid methacrolein and liquid methanol. The obtained liquid mixture (III) is then withdrawn from the bottom portion of the absorption tower.

There is no limitation with respect to the type of the absorption tower used in the method of the present invention, and any conventional distillation tower, such as a plate tower or a packed tower, can be used. However, since methacrolein, which is introduced into the absorption tower, is an easily polymerizable compound, it is preferred to use a tower having a structure such that the clogging with the polymerized products does not occur or having a structure such that, even when the clogging with the polymerized products occurs, the polymerized products can be easily removed. Specific examples of absorption towers include a plate tower provided with a sieve tray, a cascade tray, a turbogrid tray, a ripple tray or the like, and a packed tower which is regularly packed with packing materials, such as Mellapak and Sulzer packing (each manufactured and sold by Sumitomo Heavy Industries, Ltd., Japan). It is preferred that the contact of liquid mixture (II) with the dehydrated gas mixture (b) in the absorption tower is conducted at a temperature of from −25 to 10° C. under a pressure of from 0.2 to 3.0 kg/cm$^2$.

In the method of the present invention, it is preferred that the contents of the liquid methacrolein and the liquid methanol in the liquid mixture (II) are 5 to 60% by weight and 40 to 95% by weight, respectively, more advantageously, 10 to 50% by weight and 40 to 75% by weight, respectively, based on the weight of the liquid mixture (II). In the method of the present invention, as the liquid mixture (II) which is introduced into the absorption tower, use can be made of a liquid mixture (IV) containing liquid methacrolein and liquid methanol, which liquid mixture (IV) is obtained by separation from the reaction mixture (containing methyl methacrylate, water, methacrolein and methanol) obtained by the direct ML-to-MMA synthesis reaction, that is, the liquid mixture (IV) may be recycled to the absorption tower as the liquid mixture (II).

In the method of the present invention, it is preferred that the water content of the liquid mixture (II) is as low as possible. Specifically, it is preferred that the water content of the liquid mixture is 0.5% by weight or less, more advantageously 0.2% by weight or less. When the liquid mixture (IV) is used as the liquid mixture (II), the water content of the liquid mixture (IV) always falls within the above-mentioned desirable range by a method in which a reaction mixture (containing methyl methacrylate, water, methacrolein and methanol) obtained by the direct ML-to-MMA synthesis reaction is introduced into a distillation tower which is shown in FIG. 3, followed by a conventional distillation operation.

Further, the liquid mixture (II) may contain compounds other than methacrolein and methanol as long as the compounds do not adversely affect the direct ML-to-MMA synthesis reaction. For example, the liquid mixture (IV)

generally contains small amounts of by-products formed in the methacrolein synthesis reaction. The liquid mixture (IV), which may be introduced into the absorption tower as the liquid mixture (II), generally contains, in addition to the above-mentioned by-products, 1 to 25% by weight of methyl methacrylate and small amounts of by-products formed in the direct ML-to-MMA synthesis reaction. Representative examples of by-products include acetone, methyl formate, methyl acetate and methyl acrylate. The presence of these by-products in the liquid mixture (II) only causes the contents of methacrolein and methanol of the liquid mixture (III), which is subjected to the direct ML-to-MMA synthesis reaction, to be slightly lowered and does substantially not adversely affect the direct ML-to-MMA synthesis reaction.

As mentioned later, when the content of methacrolein in the liquid mixture (III) is too high, not only is the catalytic activity of the palladium catalyst lowered, but also the selectivity for methyl methacrylate in the direct ML-to-MMA synthesis becomes low. Therefore, when the content of methacrolein in the liquid mixture (III) produced by introducing the liquid mixture (II) into the absorption tower is too high, it is preferred that methanol is added to the liquid mixture (II) and then introduced into the absorption tower, instead of the liquid mixture (II). In this case, it is preferred that the content of the methacrolein in the liquid mixture (III) is not lower than the desired level for the direct ML-to-MMA synthesis reaction (i.e. the content of the methacrolein in the liquid mixture (III) is not less than 25% by weight, based on the weight of the liquid mixture (III), and the weight ratio of the methacrolein to the methanol in the mixture (III) is not less than 0.33).

In the method of the present invention, the preferred amount of the liquid mixture (II) to be introduced into the absorption tower varies depending on various absorption conditions in the absorption tower in which the contact of the liquid mixture (II) with methanol containing gas is conducted [such as the temperature and pressure in the absorption tower and the amount of gas (b) introduced into the absorption tower]. However, it is preferred that the amount of the liquid mixture (II) is from 50 to 1000 g, more advantageously 100 to 500 g, per $Nm^3$ of the dehydrated gas mixture (b).

By subjecting the methacrolein and methanol, which are contained in the liquid mixture (III) obtained in the above-mentioned manner, to an oxidative esterification reaction (the direct ML-to-MMA synthesis reaction) in the presence of molecular oxygen and in the presence of a palladium catalyst, methyl methacrylate is produced in the form of a reaction mixture containing methyl methacrylate, water, methacrolein and methanol.

The water content of the liquid mixture (III) is preferably 2% by weight or less, more preferably 1.5% by weight or less, still more preferably 1.0% by weight or less. It is also preferred that the content of methacrolein in the liquid mixture (III) is 25% by weight or more, and the weight ratio of methacrolein to methanol in the liquid mixture (III) is 0.33 or more. The upper limit of the content of methacrolein in the liquid mixture (III) is an amount corresponding to the stoichiometric ratio of methacrolein to methanol in the direct ML-to-MMA synthesis reaction. However, too high a content of methacrolein in the liquid mixture (III) brings about not only a lowering of the activity of the palladium catalyst but also a lowering of the selectivity for methyl methacrylate. In general, it is preferred that the content of methacrolein in the liquid mixture (III) is 69% by weight or less, and the weight ratio of methacrolein to methanol in the liquid mixture (III) is 2.2 or less. Therefore, when the liquid mixture (III) has an excess content of methacrolein, it is desirable that the liquid mixture (III) is diluted with methanol or a liquid mixture containing methanol so as to adjust the content of methacrolein and the methacrolein/methanol weight ratio to values within the above-mentioned preferred ranges.

The method for synthesizing methyl methacrylate by an oxidative esterification reaction (the direct ML-to-MMA synthesis reaction) may be appropriately selected from known methods disclosed, for example, in Examined Japanese Patent Application Publication (Japanese Kokoku) Nos. 57-035856, 57-035857, 57-035859, 62-007902 and 5-069813 (Japanese Patent Application Publication Nos. 57-035856, 57-035857 and 57-035859 correspond to U.S. Pat. No. 4,249,019. Japanese Patent Application Publication No. 62-007902 corresponds to Australian Patent No. 518 930.).

As the palladium catalyst to be used in the method of the present invention, a carrier-supported catalyst can be used which comprises palladium and lead.

In addition to palladium and lead, the palladium catalyst may also contain a heteroelement, for example, mercury, thallium, bismuth, tellurium or the like. It is preferred that the catalyst contains 5% by weight or less, more advantageously 1% by weight or less, of the heteroelement.

Further, the palladium catalyst may also contain at least one compound selected from the group consisting of an alkali metal compound and an alkaline earth metal compound. It is preferred that the catalyst contains 0.01 to 30% by weight, more advantageously 0.01 to 5% by weight, of at least one compound selected from the group consisting of an alkali metal compound and an alkaline earth metal compound. The incorporation of the alkali metal compound and/or the alkaline earth metal compound into the catalyst can be performed by a method in which such a compound is added to a solution containing a palladium compound or a lead compound, and a carrier is treated with the solution, thereby adsorbing or adhering the alkali metal compound and/or the alkaline earth metal compound onto the carrier, together with the palladium compound or the lead compound. Alternatively, a carrier having, supported thereon, an alkali metal compound and/or an alkaline earth metal compound can be used for producing a catalyst. Instead of using a carrier, a solution containing an alkali metal compound and/or an alkaline earth metal compound can be added to a reaction system of the direct ML-to-MMA synthesis reaction.

The carrier can be selected from a wide variety of materials, such as activated carbon, silica, alumina, silica-alumina, zeolite, magnesia, silica-alumina-magnesia, and the like.

There is no particular limitation on the amount of the palladium supported on a carrier, but the amount is preferably 0.1 to 20% by weight, more preferably 1 to 10% by weight, based on the weight of the carrier. There is no limitation on the amount of the lead supported on a carrier, but the amount is preferably 0.05 to 17% by weight, more preferably 0.45 to 8.5% by weight, based on the weight of the carrier. The atomic ratio of palladium to lead is preferably in the range of from 3/0.7 to 3/1.3, more preferably in the range of from 3/0.9 to 3/1.1.

The amount of the catalyst to be used varies depending on the composition of the feedstock and of the catalyst, the reaction conditions, the reaction modes, and the like. However, when the catalyst is used in a slurry form, it is preferred to use the catalyst in an amount of 0.04 to 0.5 kg per liter of the reaction system solution.

The direct ML-to-MMA synthesis reaction can be performed by any of conventional reaction modes, such as gas phase reaction, liquid phase reaction and trickle bed reaction. For example, when the direct ML-to-MMA synthesis reaction is conducted by liquid phase reaction, any known reactor, such as a bubble column reactor, a draft tube reactor or an agitation type reactor, can be employed.

In the direct ML-to-MMA synthesis reaction, molecular oxygen is used. Molecular oxygen may be in the form of an oxygen gas or a gas mixture of an oxygen gas and an inert diluent gas, such as nitrogen gas or carbon dioxide gas. Molecular oxygen may be provided in the form of air.

When the above reaction is conducted continuously, deterioration of the palladium catalyst can be suppressed by conducting the reaction while adding a solution of a lead compound to the reactor. The concentration of lead in the solution of a lead compound varies depending on the composition of the feedstock and of the catalyst, the reaction conditions and the reaction modes. However, by supplying a lead compound to the reactor in an amount which is selected in accordance with the oxygen partial pressure of the gas discharged from the gas outlet of the reactor, the palladium/lead atomic ratio of the palladium catalyst can be kept stably in the range of from 3/0.7 to 3/1.3 during the reaction. For example, the amount of the lead compound to be added can be selected by a method in which the oxygen partial pressure of the gas discharged from the gas outlet of the reactor is set at 0.02 to 0.8 $kg/cm^2$, and the concentration of lead in the solution of a lead compound is reduced to a minimum value which can maintain the above-mentioned range of oxygen partial pressure and is in the range of from 0.1 to 2,000 ppm by weight. The lower the set oxygen partial pressure, the lower the concentration of lead in the solution can be. When the amount of the lead compound is too large, disadvantages are caused in that the treatment cost for detoxifying the lead contained in the waste water from the process for methyl methacrylate production becomes high and the by-production of methyl formate is increased. For obviating such disadvantages, it is preferred to reduce the amount of the lead compound by lowering the oxygen partial pressure at the gas outlet of the reactor to 0.4 $kg/cm^2$ or less, more preferably 0.2 $kg/cm^2$ or less. However, when the oxygen partial pressure is too small, problems arise, such as a lowering of the conversion of methacrolein and the formation of unfavorable by-products. Therefore, it is preferred to choose an oxygen partial pressure which can prevent the above-mentioned problems caused by a lack of oxygen. The oxygen concentration of the gas discharged from the gas outlet of the reactor should be controlled to a level not exceeding the explosion limit (8% by volume).

The reaction pressure can be selected from a wide range of from reduced pressures to superatmospheric pressures, but is generally from 0.5 to 20 $kg/cm^2$.

It is preferred to maintain the reaction system at a pH of 6 to 9 by adding thereto at least one compound selected from the group consisting of an alkali metal compound and/or an alkaline earth metal compound, such as oxide, hydroxide, carbonate, carboxylate and the like.

When the concentration of methacrolein is high, the reaction can be carried out even at a temperature higher than 100° C. However, a reaction temperature of from 30 to 100° C. is preferred, and a reaction temperature of from 60 to 90° C. is more preferred.

The reaction time varies depending on other reaction conditions, but is generally in the range of from 1 hour to 20 hours.

By conducting the direct ML-to-MMA synthesis reaction under the above conditions, a reaction mixture containing methyl methacrylate as a main reaction product is obtained. In addition to methyl methacrylate, the obtained reaction mixture also contains unreacted methacrolein and unreacted methanol, and small amounts of water and methacrylic acid as by-products. The reaction mixture further contains trace amounts of by-products, such as methyl formate, methyl isobutyrate, isobutylaldehyde, methyl acetate, methyl acrylate and the like.

When the above-mentioned reaction mixture obtained by the direct ML-to-MMA synthesis reaction is subjected to distillation by introducing the reaction mixture into a distillation tower (designated as J in FIG. 3) at a middle portion thereof, an azeotropic mixture of methacrolein and methanol (azeotropic point: 58° C. as measured under the normal pressure, i.e., 1 atm.; methanol/methacrolein =45.7 mole %/54.3 mole %) is distilled from an upper portion of the distillation tower. In this instance, when excess methanol is present in the distillation tower, the excess methanol and a part of methyl methacrylate (produced by the direct ML-to-MMA synthesis reaction) forms an azeotropic mixture (azeotropic point: 64.5° C. as measured under the normal pressure, i.e., 1 atm.; methanol/methyl methacrylate=93.4 mole %/6.6 mole %) and the formed azeotropic mixture is distilled together with the above-mentioned methacrolein/methanol azeotropic mixture. The liquid distilled from the upper portion of the distillation tower is the liquid mixture (IV) containing liquid methacrolein and liquid methanol. If desired, the liquid mixture (IV) can be recycled and introduced into the above-mentioned dehydration tower as the liquid mixture (I) and/or into the absorption tower as the liquid mixture (II).

In the above-mentioned distillation operation, when the above-mentioned azeotropic mixture of methanol and methyl methacrylate is formed, the liquid mixture (IV) (containing liquid methacrolein and liquid methanol) further contains methyl methacrylate. Therefore, when the liquid mixture (IV) further containing methyl methacrylate is introduced into the dehydration tower at an upper portion thereof as liquid mixture (I) and/or into the absorption tower at an upper portion thereof as liquid mixture (II), methyl methacrylate contained in the liquid mixture (IV) is inevitably introduced into the dehydration tower and/or the absorption tower; however, this would not cause any serious problem.

On the other hand, from the bottom of the distillation tower, a liquid mixture containing liquid methyl methacrylate and water is obtained. This liquid mixture is purified by a conventional method to thereby obtain methyl methacrylate. For example, the purification for obtaining high purity methyl methacrylate can be conducted by a method in which the methyl methacrylate/water liquid mixture is introduced into a phase separation vessel, so that the liquid mixture separates into an upper layer containing methyl methacrylate and a lower layer containing water; and the upper layer containing methyl methacrylate is introduced into a distillation tower (other than the above-mentioned distillation tower used for the distillation of the reaction mixture obtained by the direct ML-to-MMA synthesis reaction) to distill off high boiling point compounds and low boiling point compounds, thereby separating methyl methacrylate. Although the methyl methacrylate/water liquid mixture further contains the above-mentioned trace amounts of by-products (such as methyl isobutylate, isobutylaldehyde, methyl acetate and methyl acrylate), these by-products are separated and removed during the purification process for methyl methacrylate.

Some of the above-mentioned trace amounts of by-products are also contained in the above-mentioned liquid mixture (IV) containing liquid methacrolein and liquid methanol. Therefore, when the liquid mixture (IV) is recycled and introduced into the dehydration tower as the liquid mixture (I) and/or into the absorption tower as the liquid mixture (II), trace amounts of by-products are inevitably introduced into the dehydration tower and/or the absorption tower; however, the trace amounts of by-products do not adversely affect the dehydration operation and the absorption operation. Further, the distillation operation for separating the liquid mixture (IV) is not affected by the presence of the trace amounts of by-products in the reaction mixture obtained by the direct ML-to-MMA synthesis reaction.

In the present invention, with respect to the type of the distillation tower (designated as J in FIG. 3) used for obtaining the liquid mixture (IV) and the methyl methacrylate/water liquid mixture from the upper portion thereof and from the bottom thereof, respectively, there is no particular limitation, and any conventional distillation tower, such as a plate tower or a packed tower, can be used. However, since methacrolein, methyl methacrylate and methacrylic acid, which are introduced into the distillation tower, are easily polymerizable compounds, it is preferred to use a tower having a structure such that clogging with the polymerized products does not occur, or having a structure such that, even when the clogging with the polymerized products occurs, the polymerized products can be easily removed. Specific examples of distillation towers include a plate tower provided with a sieve tray, a cascade tray, a turbogrid tray, a ripple tray or the like, and a packed tower which is regularly packed with packing materials, such as Mellapak and Sulzer packing (each manufactured and sold by Sumitomo Heavy Industries, Ltd., Japan).

In the method of the present invention, an appropriate distillation temperature in the distillation tower (designated as J in FIG. 3) varies depending on the distillation pressure, the composition of the liquid in the distillation tower, the number of trays in the distillation tower and the like. However, in order to suppress the generation of the above-mentioned polymerized products (derived from methacrolein, methyl methacrylate or methacrylic acid, which are easily polymerizable compounds) and the generation of high boiling point compounds (which causes the loss of methacrolein monomers or methyl methacrylate monomers) to a minimum level, it is preferred that the distillation temperature is as low as possible. However, when the distillation temperature is too low, disadvantages are likely to be caused such that the distillation pressure also becomes low, so that it becomes necessary to use the distillation tower having a disadvantageously large size, and that it becomes necessary to use a coolant for concentrating the gas phase at the uppermost portion of the distillation tower. Specifically, with respect to the distillation conditions, the distillation temperature or the temperature of the liquid at the bottom portion of the distillation tower is preferably within the range of from 70 to 100° C., more preferably from 70 to 85° C., and the distillation pressure is preferably within the range of from a reduced pressure of 500 Torr to 2 kg/cm$^2$.

As mentioned above, methacrolein, methyl methacrylate and methacrylic acid, which are easily polymerizable, are introduced into the distillation tower (designated as J in FIG. 3) used for obtaining the liquid mixture (IV) and the methyl methacrylate/water liquid mixture from the upper portion thereof and from the bottom thereof, respectively. Therefore, it is preferred that a polymerization inhibitor is added to the liquid phase in the distillation tower in an amount of from 10 to 1000 ppm by weight. When the liquid mixture (IV) containing liquid methacrolein and liquid methanol is recycled and introduced into the dehydration tower at an upper portion thereof and/or absorption tower at an upper portion thereof, the above-mentioned polymerization inhibitor also serves to suppress the polymerization of methacrolein in the pipes used for recycling the liquid mixture (IV). Examples of polymerization inhibitors generally employed include hydroquinone and phenothiazine.

One embodiment of the method of the present invention will now be described with reference to FIGS. 1 and 3.

As shown in FIG. 1, at least one starting material selected from the group consisting of isobutylene and tert-butanol is subjected to a gas phase catalytic oxidation reaction with molecular oxygen in the presence of a catalyst to thereby obtain a gas (a)(1) containing methacrolein gas and steam, and the obtained gas (a)(1) is introduced into a bottom portion of a quenching tower (A) so as to cool the gas (a)(1) by contact with quenching water (2) supplied to a lower portion of the quenching tower (A), thus causing the steam in the gas (a)(1) to be condensed to thereby produce water. The water produced is discharged out of the quenching system from a bottom portion of the quenching tower (A) as waste water (3). High boiling point by-products contained in the gas (a)(1) (water-soluble organic acids, such as methacrylic acid, acrylic acid, acetic acid and maleic acid which are by-produced in the methacrolein synthesis reaction; and furfural and terephthalic acid and the like which are produced by cyclodimerization of the by-produced organic acids, synthesized methacrolein and the like) are also discharged out of the quenching system together with the waste water (3). By this quenching, the gas (a) is rapidly cooled to a temperature which is preferably in the range of from room temperature to 95° C., more preferably from 30 to 80° C.

The thus quenched gas (a) ascends toward the uppermost portion of the quenching tower (A) while contacting countercurrently with quenching water (2') which flows downwardly from an upper portion of the quenching tower (A). By the countercurrent contact with quenching water (2'), the gas (a) is further cooled to the extent that, when the internal pressure of the quenching tower (A) is 1.0 kg/cm$^2$, the temperature of the gas (a) at the uppermost of the quenching tower (A) becomes preferably from 30 to 60° C., more preferably from 40 to 50° C. Then, the thus treated gas (a) is introduced into a lower portion of the dehydration tower (B) as a partially dehydrated gas (4) containing methacrolein and steam.

On the other hand, the liquid mixture (I)(5) containing liquid methacrolein and liquid methanol is introduced into an upper portion of the dehydration tower (B) and allowed to flow downwardly therein and contact countercurrently with the partially dehydrated gas (4). By the countercurrent contact with the gas (4), substantially all of the liquid mixture (I)(5) is gasified to thereby form a gas mixture (I') containing methacrolein gas and methanol gas. At this time, the steam in the partially dehydrated gas (4) is deprived of the latent heat of gasification and hence is caused to be condensed to produce water, and the produced water flows down to the bottom of the dehydration tower (B) and is discharged from the bottom of the dehydration tower (B) as separated water (6). By this dehydration, the partially dehydrated gas (4) is converted to a dehydrated gas (a') containing methacrolein, and the gas (a') is withdrawn together with the gas mixture (I') as a dehydrated gas mixture (b)(7) from the uppermost portion of the dehydration tower (B), and the dehydrated gas mixture (b)(7) is introduced into a lower portion of the absorption tower (C).

The separated water (6) withdrawn from the bottom of the dehydration tower (B) can be discharged as such out of the dehydration system. However, it is preferred that the separated water (6) is used as the quenching water (2). That is, when the separated water (6) is used as the quenching water (2), most of the methanol, methacrolein and methyl methacrylate which are contained in small amounts in the separated water (6) are gasified and then entrained by the gas (a), thereby enabling the methanol, methacrolein and methyl methacrylate to be recovered.

In FIG. 1 showing an example of a system for practicing the above embodiment of the method of the present invention, the quenching tower (A) and the dehydration tower (B) are depicted as separately provided two towers. However, it is also possible that a lower part and an upper part of a single tower are used as a quenching tower (A) and a dehydration tower (B), respectively.

The dehydrated gas mixture (b)(7) obtained from the uppermost portion of the dehydration tower (B) is introduced into a lower portion of the absorption tower (C). In the absorption tower (C), the gas (b) is allowed to contact countercurrently with the liquid mixture (II)(9) containing liquid methacrolein and liquid methanol, which is introduced from an upper portion of the absorption tower (C). By this counter-current contact, the gas (b) is caused to be absorbed by the liquid mixture (II)(9) to thereby obtain the liquid mixture (III)(8), which is withdrawn from the bottom portion of the absorption tower (C).

A gas containing a trace amount of methacrolein, which has not been absorbed by the liquid mixture (II), is discharged as vent gas (10) from the uppermost portion of the absorption tower (C). This vent gas contains nitrogen, oxygen, by-produced carbon dioxide, unreacted isobutylene, unreacted methacrolein and the like. Of these compounds, those which can be converted to carbon dioxide are converted to it, and the obtained carbon dioxide is used as a part of the diluent for the methacrolein synthesis reaction. The liquid mixture (III)(8) withdrawn from the bottom portion of the absorption tower (C) is used as a feedstock for the direct ML-to-MMA synthesis reaction.

When the methacrolein content of the liquid mixture (III)(8) corresponds to an amount which is larger than the stoichiometric amount in the direct ML-to-MMA synthesis reaction, the methacrolein content may optionally be adjusted to a desired level by dilution with methanol, a liquid mixture of methanol and methacrolein or a liquid mixture of methanol, methacrolein and methyl methacrylate.

The liquid mixture (III)(8) obtained as mentioned above is introduced into an oxidative esterification reactor (the direct ML-to-MMA synthesis reactor)(D). In the direct ML-to-MMA synthesis reactor (D), the liquid methacrolein and liquid methanol, which are contained in the liquid mixture (III)(8), are subjected to an oxidative esterification reaction in the presence of molecular oxygen and in the presence of a palladium catalyst, to thereby produce methyl methacrylate in the form of a reaction mixture containing methyl methacrylate, water, methacrolein and methanol.

Further, if desired, as shown in FIG. 3, a reaction mixture (containing methyl methacrylate, water, methacrolein and methanol)(13) obtained by the direct ML-to-MMA synthesis reaction may be introduced into a separation tower (distillation tower)(J) for separating the methacrolein and methanol from the reaction mixture. That is, in the separation tower (distillation tower)(J), the reaction mixture (13) may be subjected to distillation, and a liquid mixture (IV) (25) containing liquid methacrolein and liquid methanol is obtained by separation from an upper portion of the distillation tower. At the same time, a liquid mixture (24) containing liquid methyl methacrylate and water is recovered from the bottom portion of the tower (J), and low boiling point by-products (15) are discharged from the uppermost portion of the tower. The thus obtained liquid mixture (IV) can be recycled to the dehydration tower (B) and/or the absorption tower (C), and can be used as the liquid mixture (I) and/or (II).

Figure 2:
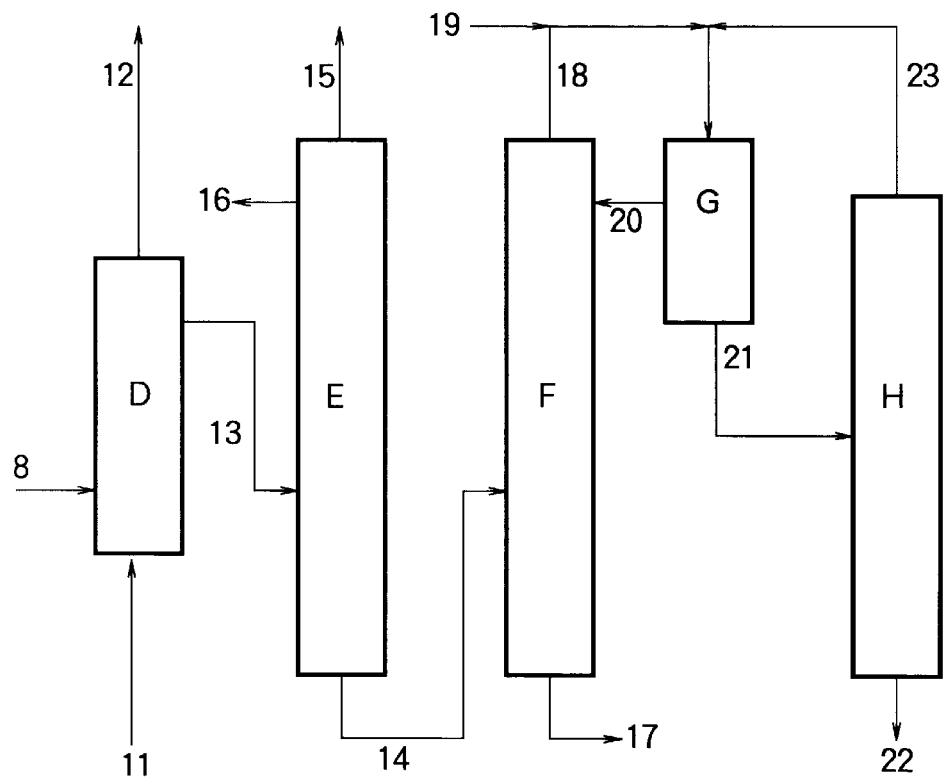
FIG. 2 is a diagram showing an example of a system used in the conventional methods for continuously performing the direct ML-to-MMA synthesis reaction, wherein methanol is separated and recovered from the reaction mixture obtained by the direct ML-to-MMA synthesis reaction.

FIG. 2 schematically shows an example of a system used in a conventional method in which the dehydration of and the absorption of methacrolein are conducted using methanol to thereby obtain a liquid mixture for the direct ML-to-MMA synthesis reaction; the obtained liquid mixture is subjected to the direct ML-to-MMA synthesis reaction to obtain a reaction mixture; and methanol is separated from the obtained reaction mixture. The above method has been constructed by combining the conventional methods as described in Unexamined Japanese Patent Application Laid-Open Specification (Japanese Kokai) Nos. 56-87530, 58-157740, 57-9739 and 57-9740.

In the system shown in FIG. 2, a reaction mixture (13) obtained by the direct ML-to-MMA synthesis reaction is introduced into an unreacted methacrolein separation tower (distillation tower) (E) at a lower portion thereof to thereby separate and recover a liquid mixture (16) containing unreacted methacrolein and unreacted liquid methanol. The liquid mixture (16) is recycled to the direct ML-to-MMA synthesis reactor.

From the top of the separation tower (E), low boiling point by-products (15) are distilled off. On the other hand, from the bottom of the separation tower (E), a liquid mixture (14) containing liquid methyl methacrylate and liquid methanol is withdrawn. The liquid mixture (14) is introduced into an unreacted methanol separation tower (F) at a lower portion thereof, while introducing a $C_6$–$C_8$ saturated hydrocarbon (19) into the separation tower (F) at an upper portion thereof, to thereby distill substantially all of the methanol in the form of an azeotropic mixture (18) thereof with the $C_6$–$C_8$ saturated hydrocarbon from the top of the separation tower (F), while recovering crude methyl methacrylate (17) from the bottom of the separation tower (F).

Then, the azeotropic mixture (18) is subjected to phase separation in a phase separation vessel (G) to thereby separate the mixture (18) into an upper layer (20) composed mainly of $C_6$–$C_8$ saturated hydrocarbon and a lower layer (21) composed mainly of methanol. The obtained upper layer (20) composed mainly of $C_6$–$C_8$ saturated hydrocarbon is recycled to the unreacted methanol separation tower (F). On the other hand, the lower layer (21) composed mainly of methanol is subjected to distillation in the unreacted methanol recovering tower (H), wherein methanol (22) is recovered from the bottom of the unreacted methanol recovering tower (H) and recycled to the dehydration tower and the absorption tower. From the top of the unreacted methanol recovering tower (H), the $C_6$–$C_8$ saturated hydrocarbon is distilled in the form of an azeotropic mixture thereof with methanol, which is recycled to the phase separation vessel (G). Thus, the separation and recovery of the unreacted methanol are performed.

In the method of the present invention, the unreacted methanol separation tower (F), the phase separation vessel (G), the unreacted methanol recovering tower (H) and the pipeline system connecting these apparatuses, which are shown in FIG. 2, are not necessary. Thus, by the method of the present invention, it has become possible to shorten and simplify the direct ML-to-MMA process for producing methyl methacrylate. This effect is very remarkable. Further, since the method of the present invention can be conducted without using the above-mentioned apparatuses and the pipeline system, the method of the present invention can be advantageously performed without suffering troubles, which inevitably accompany the conventional method and which prevent the stable operation of the production plant for methyl methacrylate, such as the cumbersome operations using the unreacted methanol recovering tower (H) in which a plurality of azeotropic systems are present; the clogging of the distillation column, which is caused by the polymerized product formed due to the change in operation conditions; and the unfavorable changes in the compositions of the phase separation products, which are caused by the substances accumulated in the production system. Thus, the method of the present invention is free from the difficulties encountered by the commercial scale practice of the conventional direct ML-to-MMA process.

Best Mode for Carrying Out the Invention

Hereinbelow, the present invention is described in more detail with reference to Examples and Comparative Examples, which should not be construed as limiting the scope of the present invention.

In the Examples and Comparative Examples, various measurements were conducted by the following methods.

a) Quantitative Analysis of Methacrolein Gas, Acetone Gas, Isobutylene Gas and Carbon Dioxide Gas Contained in a Gaseous Sample by Gas Chromatography (GC):

Measurement was conducted under the following conditions by means of the below-described apparatus.

i) Chromatograph: GC-3BT (Manufactured and Sold by Shimadzu Corporation, Japan)

ii) Column

Support: Porapak-QS (manufactured and sold by Waters Assoc. Co., USA)

Packing length of column: 5 m

Column temperature: 75° C.

Carrier gas: helium

Detector: thermal conductivity detector (TCD)

b) Quantitative Analysis of Oxygen Gas, Nitrogen Gas and Carbon Monoxide Gas Contained in a Gaseous Sample by GC:

Measurement was conducted under the following conditions by means of the below-described apparatus.

i) Chromatograph: GC-3BT (Manufactured and Sold by Shimadzu Corporation, Japan)

ii) Column

Support: Molecular Sieve 5A (manufactured and sold by Shimadzu Corporation, Japan)

Packing length of column: 3 m

Column temperature: 70° C.

Carrier gas: argon

Detector: TCD c) Quantitative Analysis of Liquid Methacrolein, Liquid Methanol and Liquid Methyl Methacrylate Contained in a Liquid Sample by GC:

Measurement was conducted under the following conditions by means of the below-described apparatus.

i) Chromatograph: GC-9A (Manufactured and Sold by Shimadzu Corporation, Japan)

ii) Column

Support: Chromosorb 101 (manufactured by Manvile Corporation, USA, and sold by Shimadzu Corporation, Japan)

Packing length of column: 4 m

Column temperature: elevated from 120° C. to 180° C.

Carrier gas: helium

Detector: flame ionization detector (FID)

d) Quantitative Analysis of Liquid Methacrylic Acid Contained in a Liquid Sample by GC:

Measurement was conducted under the following conditions by means of the below-described apparatus.

i) Chromatograph: GC-4CPTF (Manufactured and Sold by Shimadzu Corporation, Japan)

ii) Column

Packing materials: Stationary liquid phase/support: FFAP20/Chromosorb W (manufactured by Shinwa Chemical industries, Ltd., Japan, and sold by Shimadzu GLC Center, Japan)

Packing length of column: 2 m

Column temperature: 145° C.

Carrier gas: helium

Detector: FID e) Water Content of a Liquid Sample

The water content of a liquid sample was determined using a Karl Fischer coulometric moisture content meter, VA-02 (manufactured and sold by Mitsubishi Chemical Industries, Ltd., Japan).

f) Conversion of Methacrolein (%)

The conversion of methacrolein (%) was calculated by the following formula: Conversion of methacrolein (%)=

$$\left(1 - \frac{\text{molar amount of methacrolein contained in the reaction mixture which was withdrawn from the oxidative esterification reactor}}{\text{molar amount of methacrolein introduced into the oxidative esterification reactor}}\right) \times 100$$

g) Selectivity for Methyl Methacrylate (%)

The selectivity for methyl methacrylate (%) was calculated by the following formula:

Selectivity for methyl methacrylate (%)=

$$\frac{\text{molar amount of methyl methacrylate contained in the reaction mixture which was withdrawn from the oxidative esterification reactor}}{\left(\begin{array}{c}\text{molar amount of methacrolein introduced into the oxidative esterification reactor}\end{array}\right) - \left(\begin{array}{c}\text{molar amount of methacrolein contained in the reaction mixture which was withdrawn from the oxidative esterification reactor}\end{array}\right)} \times 100$$

The following Examples and Comparative Examples are described with reference to FIGS. 1, 2 and 3 in the accompanying drawings.

EXAMPLE 1

Isobutylene was subjected to a gas phase catalytic oxidation reaction with molecular oxygen in the presence of a catalyst in accordance with a conventional method to thereby prepare gas (a) (1) containing methacrolein and steam. The prepared gas (a) (1) was introduced into a quenching tower (A) to remove therefrom a large portion of the steam, and by-produced high boiling point substances and acids, by cooling the gas to a temperature of 44° C. by means of quenching water (2, 2'), to thereby partially dehydrate the gas (a) (1). The resultant partially dehydrated gas (4) had the following composition: 4.8 mole % of methacrolein, 2.7 mole % of water, 92.3 mole % in total of nitrogen, oxygen, carbon dioxide and carbon monoxide gases and unreacted isobutylene, and 0.2 mole % of by-products, such as acetone, wherein the $H_2O$/methacrolein weight ratio was 0.14.

The partially dehydrated gas (4) was fed into the bottom portion of a 30-stage plate dehydration tower (B) of 10 cm in inner diameter and 5 m in height provided with sieve trays at a flow rate of 3.6 $Nm^3$/hr, whereas a solution prepared by adding 100 ppm by weight of hydroquinone to liquid mixture (I) (5) containing liquid methacrolein and liquid methanol was fed into the dehydration tower (B) at the top plate thereof at a flow rate of 200 g/hr. The composition of liquid mixture (I) (5) was as follows: 30.0% by weight of methacrolein and 69.8% by weight of methanol, wherein the $H_2O$/methacrolein weight ratio was 0.006. The dehydration tower (B) was operated under conditions such that the temperature of the gas in the bottom portion of the dehydration tower (B) was 44° C., the temperature of the gas in the uppermost portion of the dehydration tower (B) was 18° C., the temperature of the solution was 25° C., and the pressure in the uppermost portion of the dehydration tower (B) was 1.5 $kg/cm^2$. In the dehydration tower (B), the steam contained in the partially dehydrated gas (4) was condensed to thereby produce water (6), and the water (6) was separated and discharged from the bottom portion of the dehydration tower (B). As a result, a dehydrated gas mixture (b) (7) containing methacrolein gas and methanol gas was obtained from an uppermost portion of the dehydration tower (B).

The dehydrated gas mixture (b) (7) had a composition such that the $H_2O$/methacrolein weight ratio was 0.015 and the methacrolein/methanol weight ratio was 4.3. The amount of methacrolein contained in the separated water (6) was 0.7% by weight of the amount of methacrolein produced by the gas phase catalytic oxidation reaction.

Subsequently, the dehydrated gas mixture (b) (7) obtained above was fed into the bottom portion of a 30-stage plate adsorption tower (C) of 10 cm in inner diameter and 5 m in height provided with sieve trays, whereas a solution prepared by adding 100 ppm by weight of hydroquinone to liquid mixture (II) (9) containing liquid methacrolein and liquid methanol was fed into the absorption tower (C) at the top plate thereof at a flow rate of 900 g/hr. The composition of liquid mixture (II) (9) was the same as that of the above-mentioned liquid mixture (I) (5). The absorption tower (C) was operated under conditions such that the temperature of the liquid in the bottom portion of the absorption tower (C) was −6° C., the temperature of the liquid on the top plate was −3° C., the temperature of the above-mentioned solution was −3° C., and the pressure in the uppermost portion of the absorption tower (C) was 1.4 $kg/cm^2$. In the absorption tower (C), substantially all of the methacrolein gas and methanol gas which were contained in the dehydrated gas mixture (b) (7) was absorbed by liquid mixture (II) (9), thereby obtaining liquid mixture (III) (8) containing liquid methacrolein and liquid methanol from the bottom portion of the absorption tower (C).

Liquid mixture (III) (8) had the following composition: 53.6% by weight of methacrolein, 44.9% by weight of methanol, 0.7% by weight of water, and 0.8% by weight of by-products, such as acetone.

300 g of a palladium catalyst [comprising a silica-alumina-magnesia carrier and, supported thereon, palladium (Pd) and lead (Pb); the Pd/carrier ratio was 5% by weight and the Pd/Pb atomic ratio was 3/1.03] was charged into a stainless, external circulation type bubble column reactor (D) having a volume of 1.2 liters for liquid phase, and the above-obtained liquid mixture (III) (8) was fed into the reactor at a flow rate of 450 g/hr. In this instance, a solution of sodium hydroxide in methanol and a solution of lead acetate in methanol were also fed into the reactor (D) so that the liquid in the reactor had a pH value of 6.1 and a lead concentration of 20 ppm by weight. An oxidative esterification reaction of methacrolein was conducted at a temperature of 80° C. under a pressure of 3.0 $kg/cm^2$, wherein the oxygen partial pressure of the exhausted gas (12) flowing out from the outlet of the reactor (D) was 0.095 kg/cm2. As a result, a reaction mixture (13) containing methyl methacrylate, water, methacrolein and methanol was obtained from the outlet of the reactor (D), and it was found that the conversion of methacrolein was 55.5% and the selectivity for methyl methacrylate was 86.4%.

EXAMPLE 2

The production of methyl methacrylate was conducted in substantially the same manner as in Example 1, except that the below-mentioned liquid mixture (IV) (25) containing liquid methacrolein and liquid methanol, which was obtained by separation from the reaction mixture (13) containing methyl methacrylate, water, methacrolein and methanol obtained by an oxidative esterification reaction, was recycled and introduced into the dehydration tower as the liquid mixture (I) (5) and into the absorption tower as the liquid mixture (II) (9), respectively.

The reaction mixture (13) containing methyl methacrylate, water, methacrolein and methanol, described in detail below, was fed into a 45-stage plate distillation tower (J) of 10 cm in inner diameter and 6 m in height provided with sieve trays at a portion thereof which is located at the thirtieth stage plate counted from the top plate, thereby flowing the reaction mixture (13) downwardly in the distillation tower (J), while adding hydroquinone to the downwardly flowing reaction mixture (13) so that the hydroquinone concentration of the resultant solution became 100 ppm by weight or more. The distillation tower (J) was operated under conditions such that the temperature in the uppermost portion of the distillation tower (J) was 30° C., the temperature in the bottom portion of the distillation tower (J) was 82° C., and the pressure in the distillation tower (J) was atmospheric pressure. As a result, a liquid mixture (IV) (25) containing liquid methacrolein and liquid methanol was withdrawn from the distillation tower (J) at a portion thereof which is located at the fifth stage plate counted from the top plate. Liquid mixture (IV) (25) had the following composition: 14.1% by weight of methacrolein, 70.6% by weight of methanol, 11.7% by weight of methyl methacrylate, 3.5% by weight of liquid by-products such as acetone, and 1000 ppm by weight of water, wherein the $H_2O$/methacrolein weight ratio was 0.007.

On the other hand, the partially dehydrated gas (4), which was obtained by substantially the same manner as in Example 1, was fed into the same dehydration tower (B) as used in Example 1 in substantially the same manner as in Example 1, whereas a solution prepared by adding 100 ppm by weight of hydroquinone to liquid mixture (IV) (25) was fed into the dehydration tower (B) at the top plate thereof at flow rate of 200 g/hr. The dehydration tower was operated under conditions such that the temperature of the gas in the bottom portion of the dehydration tower (B) was 44° C., the temperature of the gas in the uppermost portion was 13° C., the temperature of the solution was 20° C., and the pressure of the uppermost portion of the dehydration tower (B) was 1.5 kg/cm². In the dehydration tower, the steam contained in the partially dehydrated gas (4) was condensed to thereby produce water (6), and the produced water (6) was separated and discharged from the bottom portion of the dehydration tower (B). As a result, dehydrated gas mixture (b) (7) containing methacrolein gas and methanol gas was obtained from an uppermost portion of the dehydration tower (B).

The dehydrated gas mixture (b) (7) had the following composition: the $H_2O$/methacrolein weight ratio was 0.014 and the methacrolein/methanol weight ratio was 4.0. The amount of methacrolein contained in the separated water (6) was 0.7% by weight of the amount of methacrolein produced by the gas phase catalytic oxidation reaction.

Subsequently, the dehydrated gas mixture (b) (7) obtained above was fed into the same absorption tower (C) as used in Example 1 in substantially the same s-a manner as in Example 1, whereas a solution prepared by adding 100 ppm by weight of hydroquinone to liquid mixture (IV) (25) containing liquid methacrolein and liquid methanol was fed into the absorption tower (C) at the top plate thereof at flow rate of 1100 g/hr. The absorption tower was operated under conditions such that the temperature of the liquid in the bottom portion of the absorption tower (C) was 0° C., the temperature of the liquid on the top plate of the absorption tower (C) was –11° C., the temperature of the solution was –10° C., and the pressure of the uppermost portion of the absorption tower (C) was 1.4 kg/cm². In the absorption tower (C), substantially all of the methacrolein gas and methanol gas which were contained in the dehydrated gas mixture (b) (7) was absorbed by liquid mixture (IV) (25), thereby obtaining liquid mixture (III) (8) containing liquid methacrolein and liquid methanol from the bottom portion of the absorption tower (C).

Liquid mixture (III) (8) had the following composition: 40.0% by weight of methacrolein, 48.5% by weight of methanol, 8.6% by weight of methyl methacrylate, 0.5% by weight of water, and 2.4% by weight of by-products, such as acetone.

300 g of a palladium catalyst [comprising a silica-alumina-magnesia carrier and, supported thereon, palladium (Pd) and lead (Pb); the Pd/carrier ratio was 5% by weight and the Pd/Pb atomic ratio was 3/0.99] was charged into a stainless, external circulation type bubble column reactor (D) having a volume of 1.2 liters for liquid phase, and the above-obtained liquid mixture (III) (8) was fed into the reactor at a flow rate of 450 g/hr. In this instance, each of a solution of sodium hydroxide in methanol and a solution of lead acetate in methanol was also fed into the reactor (D) so that the liquid in the reactor had a pH value of 6.1 and a lead concentration of 25 ppm by weight. An oxidative esterification reaction of methacrolein was conducted at a temperature of 75° C. under a pressure of 3.0 kg/cm², wherein the oxygen partial pressure of the exhausted gas (12) flowing out from the outlet of the reactor (D) was 0.105 kg/cm². As a result, a reaction mixture (13) containing methyl methacrylate, water, methacrolein and methanol was obtained from the outlet of the reactor (D), and it was found that the conversion of methacrolein was 58.4% and the selectivity for methyl methacrylate was 87.8%.

Comparative Example 1

Isobutylene was subjected to a gas phase catalytic oxidation reaction with molecular oxygen in the presence of a catalyst in accordance with a conventional method, to thereby prepare gas (a) (1) containing methacrolein and steam. The prepared gas (a) (1) was introduced into a quenching tower (A) to remove therefrom a large portion of the steam, and by-produced high boiling point substances and acids, by cooling the gas to a temperature of 35° C. by means of quenching water (2, 2'), to thereby partially dehydrate the gas (a) (1). The resultant partially dehydrated gas (4) had the following composition: 4.3 mole % of methacrolein, 6.9 mole % of water, 88.7 mole % in total of nitrogen, oxygen, carbon dioxide and carbon monoxide gases and the unreacted isobutylene gas, and 0.1 mole % in total of liquid by-products, such as acetone, wherein the $H_2O$/methacrolein weight ratio was 0.39.

The partially dehydrated gas (4) was fed into the lower portion of a dehydration tower (B) of 40 mm in inner diameter and 60 cm in height packed with Raschig rings each 3 mm in outer diameter and 4 mm in length as a packing material, which lower portion was not packed with any packing material, at a flow rate of 13 Nl/min [wherein the Nl means liter(s) as measured under the normal conditions, i.e., at 0° C. under 1 atm.]. A solution of 100 ppm by weight of hydroquinone in methanol was fed into the dehydration tower (B) at an uppermost portion thereof, which upper portion was not packed with any packing material, at a flow rate of 88 g/hr. The dehydration tower (B) was operated under conditions such that the temperature of the gas in the bottom portion of the dehydration tower (B) was 35° C., and the temperature of the gas in the uppermost portion of the dehydration tower (B) was 15° C. In the dehydration tower (B), the steam contained in the partially dehydrated gas (4) was condensed to produce water (6), and the produced water (6) was separated and discharged from the bottom portion of the dehydration tower (B). As a result, the dehydrated gas mixture (7) containing methacrolein gas and methanol gas was obtained from an uppermost portion of the dehydration tower (B). The dehydrated gas mixture (7) had an $H_2O$/methacrolein weight ratio of 0.006.

Subsequently, the dehydrated gas mixture (7) obtained above was fed into the bottom portion of a 30-stage plate Oldershaw type absorption tower (C) of 32 mm in inner diameter, whereas methanol was fed into the absorption tower (C) at a portion thereof which is located on the top plate of the absorption tower.

The absorption tower (C) was operated under conditions such that the temperature of the liquid in the bottom portion of the absorption tower (C) was 10° C., the temperature of the liquid on the top plate of the absorption tower (C) was –11° C., the temperature of methanol was –10° C., and the pressure in the uppermost portion of the absorption tower (C) was 1.03 kg/cm². In the absorption tower (C), substantially all of the methacrolein gas and methanol gas which was contained in the dehydrated gas mixture (7) was absorbed by methanol, thereby obtaining liquid mixture (8) containing liquid methacrolein and liquid methanol from the bottom portion of the absorption tower (C).

The obtained liquid mixture (8) had the following composition: 81.7% by weight of methanol, 18.0% by weight of methacrolein, 0.13% by weight of water, and 0.1% by weight in total of by-products, such as acetone.

The amounts of liquid methanol and liquid methacrolein contained in the above-mentioned separated water (6) discharged from the bottom portion of the dehydration tower (B), were, respectively, 0.6% by weight of the amount of methanol fed into the dehydration tower (B) at the top plate thereof, and 0.5% by weight of the amount of methacrolein recovered by means of the absorption tower (C).

Comparative Example 2

The reaction mixture (13) containing methyl methacrylate, water, methacrolein and methanol obtained from the reactor (D) in substantially the same manner as in Example 1 was fed into a 50-stage plate Oldershaw type distillation tower (E) of 32 mm in inner diameter at a portion thereof which is located at the thirtieth stage plate counted from the top plate of the distillation tower (E) at a flow rate of 184 g/hr, and subjected to distillation under conditions such that the temperature in the bottom portion of the distillation tower (E) was at 76° C., the temperature in the uppermost portion of the distillation tower (E) was 37° C., and the pressure in the uppermost portion of the distillation tower (E) was 760 Torr, to thereby obtain a liquid mixture (14). The obtained liquid mixture (14) had the following composition: 24.3% by weight of methyl methacrylate, 65.7% by weight of liquid methanol, 1.5% by weight of methacrylic acid, and 8.5% by weight of water.

Subsequently, a solution prepared by adding 300 ppm by weight of phenothiazine (as a polymerization inhibitor) to the liquid mixture (14) obtained above was fed into a 60-stage plate Oldershaw type distillation tower (F) of 32 mm in inner diameter at a portion thereof which is located at the twentieth stage plate counted from the top plate of the distillation tower (F) at a flow rate of 160 g/hr, and subjected to distillation under conditions such that the temperature in the bottom portion of the distillation tower (F) was 76° C., the temperature in the uppermost portion of the distillation tower (F) was 40° C., and the pressure in the uppermost portion of the distillation tower (F) was 520 Torr, whereas n-hexane was fed into the distillation tower (F) at a portion thereof which is located at the seventh stage plate counted from the top plate of the distillation tower (F) so that the amount of n-hexane in the distillation tower (F) became 45 g, and the temperature of the seventh plate of the distillation tower (F), to which n-hexane was fed, was maintained at 59° C. In this distillation, when the amount of n-hexane in the distillation tower (F) was 45 g, the n-hexane was present only in a region of the distillation tower (F) which is higher than the seventh plate of the tower (F), to which n-hexane was fed.

However, when the amount of n-hexane fed into the distillation tower (F) was increased so that the amount of n-hexane in the distillation tower (F) became 70 g, the pressure drop of the distillation tower (F) became so large that it became impossible to continue the distillation. When the distillation tower (F) was opened and observed, it was found that polymeric products were generated on the plate immediately below the seventh plate to which n-hexane was fed.

Industrial Applicability

By the method of the present invention, it has become possible to provide a methacrolein/methanol liquid mixture for an oxidative esterification reaction, which has a high methacrolein content, as compared to the methacrolein content of the methacrolein/methanol liquid mixtures provided by the conventional methods. Therefore, by the method of the present invention, methyl methacrylate can be produced with high efficiency. Further, in the method of the present invention, the amount of methanol needed for the production process for methyl methacrylate can be considerably reduced, as compared to that in the conventional methods, and the production process for methyl methacrylate can be performed without using complicated apparatuses for the separation and recovery of methanol, which are necessarily used in the conventional methods. This is advantageous not only in that the cost for the production of methyl methacrylate can be considerably reduced, but also in that the production process is free from the troubles caused by the use of the complicated apparatuses for the separation and recovery of methanol, so that the desired methyl methacrylate can be produced stably.

What is claimed is:

1. A method for producing methyl methacrylate, which comprises:
   (1) subjecting at least one starting material selected from the group consisting of isobutylene and tert-butanol to a gas phase catalytic oxidation reaction with molecular oxygen in the presence of a catalyst to thereby obtain gas (a) containing methacrolein gas and steam;
   (2) introducing said gas (a) and a liquid mixture (I) containing liquid methacrolein and liquid methanol into a dehydration tower at a lower portion thereof and at an upper portion thereof, respectively, thereby allowing said liquid mixture (I) to flow downwardly in said dehydration tower and contact countercurrently with said gas (a) in said dehydration tower, so that said liquid mixture (I) is gasified to thereby generate a gas mixture (I') containing methacrolein gas and methanol gas while causing the steam contained in said gas (a) to be condensed to thereby produce water,
   wherein the produced water is discharged from a bottom portion of said dehydration tower to thereby dehydrate said gas (a), while withdrawing the resultant dehydrated gas (a') containing the methacrolein gas, together with said gas mixture (I'), from an uppermost portion of said dehydration tower in the form of a dehydrated gas mixture (b) containing methacrolein gas and methanol gas;
   (3) introducing said dehydrated gas mixture (b) and a liquid mixture (II) containing liquid methacrolein and liquid methanol into an absorption tower at a lower portion thereof and at an upper portion thereof, respectively, thereby allowing said liquid mixture (II) to flow downwardly and contact countercurrently with said dehydrated gas mixture (b) in said absorption tower, wherein said liquid mixture (II) is introduced in an amount sufficient to absorb substantially all of the methacrolein gas and methanol gas which are contained in said dehydrated gas mixture (b), thus causing substantially all of said methacrolein gas and methanol gas of said dehydrated gas mixture (b) to be absorbed into said liquid mixture (II), to thereby obtain a liquid mixture (III) containing liquid methacrolein and liquid methanol, followed by withdrawal of said liquid mixture (III) from a bottom portion of said absorption tower; and
   (4) introducing the withdrawn liquid mixture (III) into an oxidative esterification reactor and subjecting the methacrolein and methanol, which are contained in said liquid mixture (III), to an oxidative esterification reaction in said reactor in the presence of molecular oxygen and in the presence of a palladium catalyst, to thereby produce methyl methacrylate in the form of a reaction mixture containing methyl methacrylate, water, methacrolein and methanol.

2. The method according to claim 1, wherein at least one liquid mixture selected from the group consisting of said liquid mixtures (I) and (II) is a liquid mixture (IV) containing liquid methacrolein and liquid methanol, wherein said liquid mixture (IV) is obtained by separation from said reaction mixture obtained by said oxidative esterification reaction.

3. The method according to claim 1 or 2, wherein the contact of said liquid mixture (I) with said gas (a) in said dehydration tower is conducted at a temperature of from 10 to 60° C. under a pressure of from 0.2 to 3.0 kg/cm$^2$.

4. The method according to claim 1 or 2, wherein the contact of said liquid mixture (II) with said dehydrated gas mixture (b) in said absorption tower is conducted at a temperature of from −25 to 10° C. under a pressure of from 0.2 to 3.0 kg/cm$^2$.

5. The method according to claim 1 or 2, wherein said liquid mixture (I) is introduced into said dehydration tower in an amount of from 10 to 500 g per Nm$^3$ (wherein the Nm$^3$ means m$^3$ as measured at 0° C. under 1 atm.) of said gas (a).

6. The method according to claim 1 or 2, wherein said liquid mixture (II) is introduced into said absorption tower in an amount of from 50 to 1000 g per Nm$^3$ (wherein the Nm$^3$ means m$^3$ as measured at 0° C. under 1 atm.) of said dehydrated gas mixture (b).

7. The method according to claim 1 or 2, wherein each of said liquid mixtures (I) and (II) independently contains liquid methacrolein and liquid methanol in amounts of 5 to 60% by weight and 40 to 95% by weight, respectively, based on the respective weight of said liquid mixtures (I) and (II).

8. The method according to claim 2, wherein said liquid mixture (IV) further contains methyl methacrylate in an amount not exceeding 25% by weight, based on the weight of said liquid mixture (IV).

9. The method according to claim 1 or 2, wherein the content of the liquid methacrolein in said liquid mixture (III) is from 25 to 69% by weight, based on the weight of said liquid mixture (III), and the weight ratio of the liquid methacrolein to the liquid methanol in said liquid mixture (III) is 0.33 to 2.2.

* * * * *